United States Patent [19]

Mochida et al.

[11] Patent Number: 5,004,751

[45] Date of Patent: Apr. 2, 1991

[54] HYDANTOIN DERIVATIVES

[75] Inventors: Ei Mochida, Toshima; Kimihiro Murakami, Shizuoka; Kazuo Kato, Mishima; Katsuaki Kato, Koganei; Jun Okuda; Ichitomo Miwa, both of Nagoya, all of Japan

[73] Assignee: Mochida Pharmaceutical Co., Ltd., Tokyo, Japan

[21] Appl. No.: 426,021

[22] Filed: Oct. 24, 1989

Related U.S. Application Data

[63] Continuation-in-part of Ser. No. 235,557, Aug. 24, 1988.

[30] Foreign Application Priority Data

Aug. 28, 1987 [JP] Japan ............................ 62-214549
Feb. 25, 1989 [JP] Japan ............................ 1-43422

[51] Int. Cl.$^5$ .................. C07D 233/30; A61K 31/415
[52] U.S. Cl. .................................... 514/390; 548/309
[58] Field of Search ...................... 548/309; 514/390

[56] References Cited

U.S. PATENT DOCUMENTS

| | | | |
|---|---|---|---|
| 3,384,643 | 5/1968 | Sayigh et al. ...................... | 548/301 |
| 3,534,022 | 10/1970 | Umemoto et al. .............. | 548/311 X |
| 4,575,507 | 3/1986 | Lipinski ............................ | 514/278 |
| 4,656,169 | 4/1987 | Schnur ............................. | 514/235 |
| 4,743,611 | 5/1988 | Malamas et al. ................... | 514/390 |

FOREIGN PATENT DOCUMENTS

| | | |
|---|---|---|
| 0187387 | 7/1986 | European Pat. Off. . |
| 0251784 | 1/1988 | European Pat. Off. . |
| 0305947 | 3/1989 | European Pat. Off. ............ 548/309 |
| 6097 | 6/1968 | France . |
| 2308626 | 11/1976 | France . |

OTHER PUBLICATIONS

*Chemical Abstracts*, vol. 95, No. 15, Oct. 12, 1981, Abstract No. 132725.
*Chemical Abstracts*, vol. 97, No. 1, Jul. 5, 1982, Abstract No. 6774e.
*Chemical Abstracts*, vol. 99, 1983, Abstract No. 116079f.
*Chemical Abstracts*, vol. 107, 1987, Abstract No. 59037y.
*Chemical Abstracts*, vol. 109, 1988, Abstract No. 129004c.

*Primary Examiner*—Mary C. Lee
*Assistant Examiner*—Joseph K. McKane
*Attorney, Agent, or Firm*—Oliff & Berridge

[57] ABSTRACT

The present invention relates to novel hydantoin derivatives, processes for producing said hydantoin derivatives, pharmaceutical compositions containing at least one of said hydantoin derivatives as aldose reductase inhibitors and novel intermediate compounds in the synthesis of said hydantoin derivatives.

The present invention is based on the selection of a hydantoin which is bonded by a sulfonyl group to various substituents at the 1-position of the hydantoin skeleton.

The compounds of the present invention have a strong inhibitory activity against aldose reductase. These compounds are extremely useful for the treatment and/or prevention of various forms of diabetic complications based on the accumulation of polyol metabolites.

8 Claims, No Drawings

HYDANTOIN DERIVATIVES

This is a continuation-in-part divisional application of Ser. No. 07/235,557, filed Aug. 24, 1988.

BACKGROUND OF THE INVENTION

The present invention relates to novel hydantoin derivatives, processes for producing hydantoin derivatives, pharmaceutical compositions containing at least one of said hydantoin derivatives as aldose reductase inhibitors and novel intermediate compounds in the synthesis of said hydantoin derivatives.

Cataract, peripheral neuropathy, retinopathy and nephropathy associated with diabetes mellitus result from abnormal accumulation of polyol metabolites converted from sugars by aldose reductase. For example, sugar cataract results from damage of lens provoked by change in osmotic pressure induced by abnormal accumulation of polyol metabolites converted from glucose or galactose by aldose reductase in lens. [ see J. H. Kinoshita et al., Biochim. Biophys. Acta, 158, 472 (1968) and cited references in the report ]. And some reports were submitted about undesirable effect of abnormal accumulation of polyol metabolites in lens, peripheral nerve cord and kidney of the diabetic animals [ see A. Pirie et al. Exp. Eye Res., 3, 124 (1964) L. T. Chylack Jr. et al., Invest. Opthal., 8, 401 (1969) J. D. Ward et al., Diabetologia, 6, 531 (1970) ]. Consequently, it is important to inhibit aldose reductase as strongly as possible for treating and/or preventing diabetic complications mentioned above. Although several compounds have been offered as aldose reductase inhibitors, none of them is fully sufficient in inhibitory activity against the enzyme. Therefore, it has been desired to develop new compounds having a stronger inhibitory activity against aldose reductase.

SUMMARY OF THE INVENTION

An object of the present invention is to provide novel hydantoin derivatives and salts, solvates and solvates of salts thereof.

Another object of the present invention is to provide processes for producing said novel hydantoin derivatives.

A further object of the present invention is to provide pharmaceutical compositions comprising at least one of said novel hydantoin derivatives having an inhibitory activity against aldose reductase.

A further object of the present invention is to provide novel intermediate compounds in the synthesis of said novel hydantoin derivatives.

The present inventors previously found that substituted phenylsulfonylhydantoin derivatives and naphthalenylsulfonylhydantoin derivatives had a strong inhibitory activity against aldose reductase and accomplished an invention on aldose reductase inhibitors. (JP-A Nos. 56 213518, 60 207113, 61 43770)

The present inventors previously found that sulfonylhydantoin derivatives had a strong inhibitory activity against aldose reductase and accomplished an invention on aldose reductase inhibitors (JP kokai No. 58 109418, 62 67075, 62 201873 and 1 61465). And M. S. Malamas et al. U.S. Pat. No. 4,743,611 disclosed naphthalenesulfonyl hydantoin derivatives useful as aldose reductase inhibitors. And Ohishi et al. disclosed benzofuranylsulfonyl glycine derivatives useful as drugs of treatment of diabetic complications (JP Kokai No. 62 155269).

Furthermore, the present inventors have made extensive researches on a series of compounds having an inhibitory activity against aldose reductase and found novel hydantoin derivatives having an extremely strong inhibitory activity against aldose reductase. They are extremely useful for the treatment and/or prevention of various forms of diabetic complications based on the accumulation of polyol metabolites.

DETAILED DESCRIPTION OF THE INVENTION

As a result of extensive investigations concerning development of hydantoin derivatives having a satisfactory inhibitory activity against aldose reductase, the present inventors have found that novel hydantoin derivatives represented by the general formula (I) satisfy this requirement and have accomplished the present invention.

The present invention is based on the selection of a hydantoin which is bonded by or through a sulfonyl group to various substituents at the 1-position of the hydantoin skeleton.

The present invention is directed to novel hydantoin derivatives represented by the general formula (I):

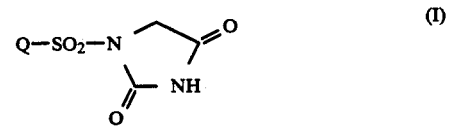

and non-toxic salts, solvates and solvates of nontoxic salts thereof; wherein Q represents an alkyl group having 1 to 8 carbon atoms, a cycloalkyl group having 3 to 6 carbon atoms, a biphenylyl group, a mono- or a fused heterocyclic group which may be substituted by one or more substituents which are same or different and selected from a group consisting of a halogen atom, a lower alkyl group, a nitro group, a cyano group, an optionally protected carboxy group, an optionally protected carboxymethyl group, a halogenated lower alkyl group, a lower alkylthio group, a lower alkylcarbonyl group, a lower alkoxy group, a lower alkylsulfinyl group, a lower alkylsulfonyl group, an optionally protected hydroxy group, an optionally protected amino group, a carbamoyl group and a phenyl group or a group:

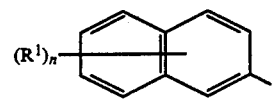

wherein $R^1$ represents an amino group which may be substituted with lower alkyl groups and/or acyl groups, a halogen atom, a lower alkyl group, an alkoxy group, a nitro group or a cyano group, or combination of any of these groups when n represents an integer of 2 or more, and n represents an integer of 1, 2, 3 or 4.

The present invention is also directed to the process for preparing above-mentioned hydantoin derivatives.

The present invention is further directed to pharmaceutical compositions characterized by containing at least one of these hydantoin derivatives as active component(s).

The present invention is further directed to novel intermediate compounds in the synthesis of abovementioned hydantoin derivatives.

Compounds of the present invention and non-toxic salts, solvates and solvates of non-toxic salts thereof represents a satisfactory inhibitory activity against aldose reductase and a preventing activity against cataracts, neuropathy in experimental animal models.

Compounds of the present invention and non-toxic salts, solvates and non-toxic salts thereof are free of central nervous system side effects such as anticonvulsant activity and low toxicity, so useful for the treatment and/or prevention of various forms of diabetic complications such as neuropathy, autonomic disease, cataract, retinopathy, neuropathy and microvascular disease.

In the hydantoin derivatives of the present invention represented by the general formula (I), it is known that the hydantoin moiety exhibits tautomerism as shown below:

having 1 to 5 carbon atoms such as formyl, acetyl, propanoyl, butanoyl, pivaloyl, etc.

In the compounds of the present invention represented by the general formula (I), the heterocyclic group can be defined as a monocyclic heterocyclic group such as pyrrolyl, pyrrolinyl, imidazolyl, pyrazolyl, triazolyl, tetrazolyl, oxazolyl, isoxazolyl, oxadiazolyl, thiazolyl, isothiazolyl, thiazolinyl, thiadiazolyl, thiatriazolyl, thienyl (thiophenyl), furyl, pyrrolidinyl, imidazolidinyl, thiazolidinyl, pyridyl or its N-oxide, pyrazinyl, pyrimidinyl, pyridazinyl, piperidyl, piperazinyl, morpholinyl, triazinyl, etc., or a fused heterocyclic group such as indolyl, isoindolyl, benzimidazolyl, quinolyl, isoquinolyl, quinazolinyl, cinnolinyl, phthalazinyl, quinoxalinyl, indazolyl, benzotriazolyl, benzoxazolyl, benzoxadiazolyl, benzothiazolyl, benzothiadiazolyl, benzisoxazolyl, benzisothiazolyl, benzothiophenyl (benzo[b]thiophenyl or benzo[c]thiophenyl) (benzothienyl (benzo[b]thienyl or benzo[c]thienyl)), tetrahydrobenzothiophenyl (tetrahydrobenzothienyl), benzofuranyl

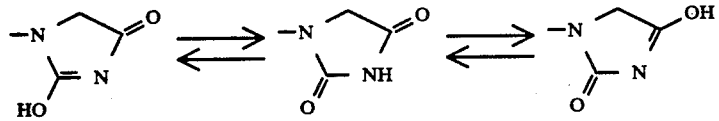

Since these tautomeric isomers are generally deemed to be the same substance, the compounds of the present invention represented by the general formula (I) also include all of these tautomeric isomers.

The compounds represented by the general formula (I) may form salts with base. Typical examples of salts with base of the compounds represented by the general formula (I) include pharmaceutically acceptable salts such as alkali metal salts (such as sodium salts, potassium salts, etc.), alkaline earth metal salts (such as magnesium salts, calcium salts, etc.), salts with organic bases (such as ammonium salts, benzylamine salts, diethylamine salts, etc.) or salts of amino acids (such as arginine salts, lysine salts, etc.). These salts of the compounds represented by the general formula (I) may be mono-salts or di-salts which may be salts of the hydantoin moiety and/or salts of the carboxy group contained in the Q group.

The compounds represented by the general formula (I) may also form acid addition salts. Typical example of acid addition salts of the compounds represented by the general formula (I) include pharmaceutically acceptable salts, such as salts of inorganic acids (such as hydrochlorides, hydrobromides, sulfates, phosphates, etc.), salts of organic acids (such as acetates, citrates, maleates, tartrates, benzoates, ascorbate, ethanesulfonates, toluenesulfonates, etc.) or salts of amino acids (such as aspartates, glutamates, etc.). These salts of the compounds represented by the general formula (I) may be salts of the heterocyclic moiety in the Q group.

In the compounds of the present invention represented by the general formula (I), the lower alkyl group can be defined more specifically as a straight or branched lower alkyl group having 1 to 4 carbon atoms such as methyl, ethyl, isopropyl, tertbutyl, etc. The alkoxy group can be defined more specifically as a straight or branched lower alkoxy group having 1 to 4 carbon atoms such as methoxy, ethoxy, isopropoxy, tert-butoxy, etc. The acyl group can be defined more specifically as a straight or branched lower acyl group (benzo[b]furanyl or isobenzofuranyl), chromenyl, chromanyl, coumarinyl, chromonyl, triazolopyridyl, tetrazolopyridyl, purinyl, thiazolopyrimidinyl, triazolopyrimidinyl, thiadiazolopyrimidinyl, thiazolopyridazinyl, naphthyridinyl, xanthenyl, phenoxathiinyl, phenoxazinyl, phenothiazinyl, carbazolyl, etc. preferably indolyl, benzimidazolyl, benzotriazolyl, benzothiazolyl, benzisoxazolyl, benzisothiazolyl, benzothiophenyl, tetrahydrobenzothiophenyl, benzofuranyl, coumarinyl, chromonyl, more preferably benzo[b]thiophenyl or benzo[b]furanyl. The abovementioned heterocyclic groups may be substituted with a group such as a lower alkyl group (such as methyl, ethyl, isopropyl, tert-butyl, etc.), a lower alkylcarbonyl group (such as acetyl, propanoyl, butanoyl, etc.), a lower alkoxy group (such as methoxy, ethoxy, isopropoxy, tert-butoxy, etc.), a phenyl group, a cyano group, a carbamoyl group, an optionally protected carboxy group, an optionally protected carboxymethyl group, a nitro group, a halogenated lower alkyl group (such as trifluoromethyl, pentafluoroethyl, etc.), an optionally protected hydroxy group, an optionally protected amino group, (such as acyl amino, etc.), a lower alkylthio group, a lower alkylsulfinyl group, a lower alkyl sulfonyl group or a halogen atom (such as fluoro, chloro, bromo, iodo etc.), or combination of any of these groups.

In a mono- heterocyclic group, a compound unsubstituted or substituted with 1 or 2 substituents which are the same or different and selected from a group consisting of a halogen atom or a phenyl group, is preferable.

In a fused heterocyclic group, a compound unsubstituted or substituted with 1 to 3 substituents which are the same or different and selected from a group consisting of a halogen atom, a lower alkyl group, a halogenated lower alkyl group, a lower alkylthio group or a cyano group, is preferable.

When a fused heterocyclic group is a benzo[b]furan-2-yl group which may be substituted, the said substituents are preferably 1 to 3 halogen atoms.

The compounds of the present invention represented by the formula (I) can be produced by the processes described as follows. Namely;

The starting material of sulfonyl halide represented by the formula (II):

Q—SO$_2$—Y    (II)

wherein Q has the same significance as defined above, and Y represents a halogen atom, is prepared as follows.

A compound Q-H wherein Q has the same significance as defined above and H represents a hydrogen atom is reacted with a base (such as n-butyllithium or lithium diisopropylamide, etc.) and sulfur dioxide and then reacted with a halogenating reagent (such as chlorine, bromine, phosphorus pentachloride, thionyl chloride, N-chlorosuccinimide or N-bromosuccinimide, etc.) to obtain an objective compound.

Further, Q-H wherein Q has the same significance as defined above is reacted with a halosulfonic acid (preferably chlorosulfonic acid, etc.) to obtain directly an objective compound.

Further, a sulfonic acid derivative of Q-H ( Q-SO$_2$H ) wherein Q has the same significance as defined above is reacted with sodium bicarbonate to give a corresponding salt, and then reacted with a halogenating reagent (such as phosphorus pentachloride, thionyl chloride or thionyl bromide, etc.) to obtain an objective compound.

Further, a S-benzyl derivative of Q-H ( Q—S—CH$_2$C$_6$H$_5$ ) wherein Q has the same significance as defined above is reacted with a halogenating reagent (such as chlorine, etc.) to obtain an objective compound.

Further, an amine derivative of Q-H ( Q—NH$_2$ ) wherein Q has the same significance as defined above is reacted with a nitrite salt (such as sodium nitrite, etc.), and then reacted with sulfur dioxide and a halogenating reagent (such as copper (I) chloride or copper (II) chloride, etc.) to obtain an objective compound.

The sulfonyl halide derivative, obtained above mentioned procedure is reacted with a glycine derivative represented by the formula (III):

NH$_2$CH$_2$CO—R    (III)

wherein R represents a hydroxy group, an alkoxy group or an amino group which may be substituted by an alkoxycarbonyl group, to give the corresponding sulfonylglycine derivative represented by the formula (IV):

Q—SO$_2$NHCH$_2$CO—R    (IV)

wherein Q and R have the same significance as defined above. Such a condensation reaction is carried out generally in an aqueous solution, in an organic solvent (such as dichloromethane, chloroform, dioxane, tetrahydrofuran, acetonitrile, ethyl acetate, acetone, N,N-dimethylformamide, etc.) or in a mixed solvent of an aqueous solution and an organic solvent, preferably in the presence of deacidifying agent. As the deacidifying agent, triethylamine, diethylaniline, pyridine, etc. is employed in the organic solvent system, and in the aqueous system, aqueous alkali (such as sodium carbonate, sodium bicarbonate, potassium carbonate, sodium hydroxide, etc.) is employed. The condensation reaction is carried out at temperatures ranging from about −20 to 80° C., preferably 0° C. to room temperature.

When R represents an amino group in the formula (IV), the sulfonylglycine derivative is represented by the formula (V):

Q—SO$_2$NHCH$_2$CONH$_2$    (V)

wherein Q has the same significance as defined above.

The sulfonylglycine derivative represented by the formula (V) is cyclized using a haloformic acid ester (such as methyl chloroformate, ethyl chloroformate, etc.) in the presence of a base (such as sodium hydride, potassium hydride, butyllithium, etc.) to give the corresponding hydantoin derivative of the present invention represented by the formula (I). The cyclization reaction is carried out generally in an inert solvent (such as N,N-dimethylformamide, dimethylsulfoxide, ethyl ether, tetrahydrofuran, dioxane, dichloromethane, etc.) and at temperatures ranging from about −20 to 120° C., preferably 0 to 80° C.

When R represents an amino group protected with an alkoxycarbonyl group, the sulfonylglycine derivative is cyclized in the presence of a base (such as sodium hydride etc.) to give the corresponding hydantoin derivative of the present invention represented by the formula (I).

When R represents a hydroxy group or an alkoxy group in the formula (IV), the sulfonylglycine derivative is represented by the formula (VI):

Q—SO$_2$NHCH$_2$CO—R$^1$    (VI)

wherein Q has the same significance as defined above and R$^1$ represents a hydroxy group or an alkoxy group. The sulfonylglycine derivative represented by the formula (VI) is cyclized with a thiocyanate derivative (such as ammonium thiocyanate, potassium thiocyanate, etc.) in the presence of an acid anhydride (such as acetic anhydride, propionic anhydride, etc.) and, if necessary and desired, a base (such as pyridine, triethylamine, etc.) to give the corresponding 2-thiohydantoin derivative. If necessary and desired, the cyclization reaction is carried out after hydrolysis of ester when R$^1$ represents an alkoxy group. The cyclization reaction is carried out generally in an inert solvent (such as pyridine, triethylamine, N,N-dimethylformamide, dimethylsulfoxide, etc.) and at temperatures ranging from 0 to 120 ° C., preferably room temperature to 100° C. Further, the 2-thiohydantoin derivative obtained by said cyclization is oxidized using oxidizing agent (such as nitric acid, chlorine, iodine chloride, potassium permanganate, hydrogen peroxide, dimethylsulfoxide-sulfuric acid, etc.) to give the corresponding hydantoin derivatives of the present invention represented by the formula (I).

To demonstrate the utility of the compounds of the present invention, experimental examples of representative compounds are shown below.

Compounds in the present invention

Compound 1: 1-(1-chloronaphthalen-2-ylsulfonyl)-hydantoin

Compound 2: 1-(3-chloronaphthalen-2-ylsulfonyl)-hydantoin

Compound 3: 1-(5-chloronaphthalen-2-ylsulfonyl)-hydantoin

Compound 4: 1-(6-chloronaphthalen-2-ylsulfonyl)hydantoin
Compound 5: 1-(7-chloronaphthalen-2-ylsulfonyl)hydantoin
Compound 6: 1-(8-chloronaphthalen-2-ylsulfonyl)hydantoin
Compound 7: 1-(3,6-dichloronaphthalen-2-ylsulfonyl)hydantoin
Compound 8: 1-(1-bromonaphthalen-2-ylsulfonyl)hydantoin
Compound 9: 1-(3-bromonaphthalen-2-ylsulfonyl)hydantoin
Compound 10: 1-(6-bromonaphthalen-2-ylsulfonyl)hydantoin
Compound 11: 1-(5-nitronaphthalen-2-ylsulfonyl)hydantoin
Compound 12: 1-(3-methylnaphthalen-2-ylsulfonyl)hydantoin
Compound 13: 1-(6-methyl-5-nitronaphthalen-2-ylsulfonyl)hydantoin
Compound 14: 1-(7-methylnaphthalen-2-ylsulfonyl)hydantoin
Compound 15: 1-(6-methoxy-5-nitronaphthalen-2-ylsulfonyl)hydantoin
Compound 16: 1-(benzo[b]thiophen-2-ylsulfonyl)hydantoin
Compound 17: 1-(3-chlorobenzo[b]thiophen-2-ylsulfonyl)hydantoin
Compound 18: 1-(5-chlorobenzo[b]thiophen-2-ylsulfonyl)hydantoin
Compound 19: 1-(benzo[b]furan-2-ylsulfonyl)hydantoin
Compound 20: 1-(5-chlorobenzo[b]furan-2-ylsulfonyl)hydantoin
Compound 21: 1-(5-bromobenzo[b]furan-2-ylsulfonyl)hydantoin
Compound 22: 1-(benzothiazol-2-ylsulfonyl)hydantoin
Compound 23: 1-(coumarin-6-ylsulfonyl)hydantoin
Compound 24: 1-(2,5-dichlorothiophen-3-ylsulfonyl)hydantoin
Compound 25: 1-(4,5-dibromothiophen-2-ylsulfonyl)hydantoin
Compound 26: 1-(6-chlorobenzo[b]thiophen-2-ylsulfonyl)hydantoin
Compound 27: 1-(7-chlorobenzo[b]thiophen-2-ylsulfonyl)hydantoin
Compound 28: 1-(3-isopropylbenzo[b]thiophen-2-ylsulfonyl)hydantoin
Compound 29: 1-(3-trifluoromethylbenzo[b]thiophen-2-ylsulfonyl)hydantoin
Compound 30: 1-(3-bromobenzo[b]thiophen-2-ylsulfonyl)hydantoin
Compound 31: 1-(3-methoxybenzo[b]thiophen-2-ylsulfonyl)hydantoin
Compound 32: 1-(3-methylsulfonylbenzo[b]thiophen-2-ylsulfonyl)hydantoin
Compound 33: 1-(3-cyanobenzo[b]thiophen-2-ylsulfonyl)hydantoin
Compound 34: 1-(3-bromo-7-fluorobenzo[b]thiophen-2-ylsulfonyl)hydantoin
Compound 35: 1-(2-chlorobenzo[b]thiophen-3-ylsulfonyl)hydantoin
Compound 36: 1-(4-iodobenzo[b]furan-2-ylsulfonyl)hydantoin
Compound 37: 1-(4,6-dichlorobenzo[b]furan-2-ylsulfonyl)hydantoin
Compound 38: 1-(3-bromobenzo[b]furan-2-ylsulfonyl)hydantoin
Compound 39: 1-(5-fluorobenzo[b]thiophen-2-ylsulfonyl)hydantoin
Compound 40: 1-(4-chlorobenzo[b]thiophen-2-ylsulfonyl)hydantoin
Compound 41: 1-(benzo[b]isothiazol-3-ylsulfonyl)hydantoin
Compound 42: 1-(5-nitrobenzo[b]thiophen-2-ylsulfonyl)hydantoin
Compound 43: 1-(5-carboxybenzo[b]thiophen-2-ylsulfonyl)hydantoin
Compound 44: 1-(4,5-dichlorobenzo[b]furan-2-ylsulfonyl)hydantoin
Compound 45: 1-(5,6-dichlorobenzo[b]furan-2-ylsulfonyl)hydantoin
Compound 46: 1-(3-bromo-4,6-dichlorobenzo[b]furan-2-ylsulfonyl)hydantoin
Compound 47: 1-(3-chlorobenzo[b]furan-2-ylsulfonyl)hydantoin
Compound 48: 1-(7-fluorobenzo[b]furan-2-ylsulfonyl)hydantoin
Compound 49: 1-(3-bromo-7-fluorobenzo[b]furan-2-ylsulfonyl)hydantoin Reference compounds
Compound A: 1-(naphthalene-2-ylsulfonyl)hydantoin
Compound B: sorbinil : [(S)-6-Fluoro-2,3-dihydrospiro(4H-1-benzopyran-4,4'-imidazolidine)-2', 5'-dione] (synthesized by the method of R. S. sarges et al. : see J. Med. Chem., 28, 1716 (1985))

Experimental Example 1

The inhibitory activities of hydantoin derivatives on rat lens aldose reductase were measured according to the procedure of Inagaki et al. (K. Inagaki et al., Arch. Biochem. Biophys., 216, 337 (1982)) with slight modifications. Assays were performed in 0.1 M phosphate buffer (pH 6.2) containing 0.4 M ammonium sulfate, 10 mM DL-glyceraldehyde, 0.16 mM nicotinamide adenine dinucleotide phosphate, reduced form (NADPH) and aldose reductase (0.010–0.016 units) in a total volume of 1.0 ml. To this mixture was added 10 µl of the solution of each hydantoin derivative to be tested, and the decrease in absorbance at 340 nm was measured with a spectrophotometer.

The concentrations of typical hydantoin derivatives of the present invention required to produce 50% inhibition are shown in table 1.

TABLE 1

| Compounds | $IC_{50}$ (µmol/l) |
|---|---|
| 1 | 0.29 |
| 2 | 0.16 |
| 3 | 0.19 |
| 4 | 0.14 |
| 5 | 0.39 |
| 6 | 0.46 |
| 7 | 0.24 |
| 8 | 0.094 |
| 9 | 0.35 |
| 10 | 0.17 |
| 11 | 0.10 |
| 12 | 0.14 |
| 13 | 0.027 |
| 14 | 0.35 |
| 15 | 0.038 |
| A | 0.66 |

Compounds 1 to 15 of the present invention showed stronger inhibitory activities against aldose reductase than reference compound A did. Above all, compound 13 and 15 were ten times or more potent than reference compound A.

Experimental Example 2

The inhibitory activities of hydantoin derivatives on bovine lens aldose reductase were measured according to the procedure of Inagaki et al. (K. Inagaki et al., Arch. Biochem. Biophys., 216, 337 (1982)) with slight modifications. Assay procedure was the same as described in Experimental example 1 except that bovine lens aldose reductase preparation was used instead of rat lens aldose reductase preparation.

The concentrations of the typical hydantoin derivatives of the present invention required to produce 50% inhibition are shown in table 2.

TABLE 2

| Compounds | IC$_{50}$ ($\mu$mol/l) |
|---|---|
| 13 | 0.10 |
| 15 | 0.23 |
| 16 | 0.39 |
| 17 | 0.12 |
| 18 | 0.24 |
| 20 | 0.36 |
| 21 | 0.30 |
| 22 | 0.34 |
| 23 | 0.22 |
| 24 | 0.29 |
| 25 | 0.26 |
| 26 | 0.27 |
| 27 | 0.19 |
| 28 | 0.14 |
| 29 | 0.13 |
| 30 | 0.12 |
| 31 | 0.27 |
| 32 | 0.38 |
| 33 | 0.19 |
| 34 | 0.085 |
| 35 | 0.30 |
| 36 | 0.24 |
| 37 | 0.17 |
| 38 | 0.16 |
| 39 | 0.32 |
| 40 | 0.17 |
| 41 | 0.47 |
| 42 | 0.27 |
| 43 | 0.40 |
| 44 | 0.061 |
| 45 | 0.083 |
| 46 | 0.054 |
| B | 0.65 |

Compounds 13, 15, 16 to 18, 20 to 46 of the present invention showed stronger inhibitory activities against aldose reductase than reference compound B did, which is a well known potent aldose reductase inhibitor. Compound 17, 18, 23 and 24 were as potent as compound 13 and 15, which showed strongest inhibitory activities in experimental example 1. Above all, several compounds were ten times or more potent than reference compound B.

Experimental Example 3

Hydantoin derivatives of the present invention were examined for acute toxicity. Groups of 5 ICR strain mice were orally administered with compound 7, 13 to 17, 19, 20, 21, 24, 38, 40, 44, 45, 47 to 49 of the present invention in a dose of 1 g/kg, and no change was observed in any of the groups over the oneweek period after the administration.

Since the compounds of the present invention have strong inhibitory activities against aldose reductase, show lower toxicity and show stronger preventing activities against cataracts, neuropathy in animal models than known compounds, pharmaceutical compositions containing at least on of these compounds as active component(s) are useful for the treatment and/or prevention of diabetic complications based on the accumlation of polyol metabolites.

The hydantoin derivatives provided by the present invention can be employed as pharmaceutical compositions, for example, in the form of pharmaceutical compositions containing hydantoin derivatives together with appropriate pharmaceutically acceptable carrier or medium such as sterilized water, edible oils, non-toxic organic solvents or non-toxic solubilizer such as glycerin or propylene glycol. They may be mixed with excipients, binders, lubricants, coloring agents, corrigents, emulsifying agents or suspending agents such as Tween 80 or arabic gum to prepare tablets, capsules, powders, granules, subtilized granules, syrups, eye drops, suppositories, ointments, inhalants, aqueous or oily solutions or emulsion or suspensions for injections. These agents can be administered either orally or parenterally (such as intravenous administration, intramuscular administration, subcutaneous administration, intrarectal administration, percutaneous administration or permucosal administration etc.), and the amount of administration may be in the range of 1 to 3000 mg/day, preferably 10 to 500 mg/day when the preparation is tablets, capsules, powders, injections, suppositories, syrups, inharants or ointments, 1 $\mu$g to 10 mg/day, preferably 10 $\mu$g to 1 mg/day when the preparation is eye drops, and 1 to 10% composition when the preparation is ointments, and may also be adjusted according to the patient conditions and can administered once or divided 2 to 6 times or by instillation, etc.

Hereafter the present invention will be described with references to the examples below but is not deemed to be limited thereof.

EXAMPLE 1

Preparation of 1-(1-chloronaphthalen-2-ylsulfonyl)-hydantoin (compound 1).

Step 1

Preparation of N-(1-chloronaphthalen-2-ylsulfonyl)glycine.

To a solution of potassium carbonate (21 g) and glycine (11 g) in water (300 ml) was added 1-chloronaphthalen-2-ylsulfonyl chloride (31 g) at room temperature, and the mixture was stirred under reflux for 30 minutes. After cooling to room temperature, the resultant solution was acidified with 2 N hydrochloric acid to a pH in the range of 1 to 2, and the formed precipitate was separated by filtration to give 33 g of the objective compound.

Melting point: 185.5–200.7° C.

IR (KBr, cm$^{-1}$): 3380, 1720, 1325, 1135

NMR (DMSO-d$_6$, ppm): 3.63 (2H, s), 7.59–8.51 (7H, m)

Step 2

Preparation of 1-(1-chloronaphthalen-2-ylsulfonyl)-2-thiohydantoin.

Anhydrous pyridine (19 ml), ammonium thiocyanate (17 g) and acetic anhydride (50 ml) were added to the product obtained in Step 1 (30 g), and the mixture was heated with stirring on a boiling water bath for 15 minutes. After cooling to room temperature, the resultant solution was poured into ice-water (300 ml), and the formed precipitate was separated by filtration to give 30.6 g of the objective compound.

Melting point: 268.6° C. (decomposition)

IR (KBr, cm$^{-1}$): 3150, 1790, 1765, 1380, 1190
NMR (DMSO-d$_6$, ppm): 4.93 (2H, s), 7.66–8.53 (5H, m), 8.78 (1H, s)

Step 3

Preparation of 1-(1-chloronaphthalen-2-ylsulfonyl)-hydantoin.

A mixture of the product obtained in Step 2 (20 g) and 50% (w/v) nitric acid (100 ml) was heated with stirring on a boiling water bath for 40 minutes, and the resultant solution was cooled in an ice bath. The formed precipitate was separated by filtration and washed successively with water, ethyl alcohol, methyl alcohol and dichloromethane to give 4.8 g of the objective compound.

Melting point: 258.3–260.5° C.
IR (KBr, cm$^{-1}$): 3140, 1740, 1370, 1180
NMR (DMSO-d$_6$, ppm): 4.74 (2H, s), 7.80–8.39 (6H, m), 11.77 (1H, s)

EXAMPLE 2

Preparation of 1-(1-bromonaphthalen-2-ylsulfonyl)hydantoin (compound 8).

Step 1

Preparation of N-(1-bromonaphthalen-2-ylsulfonyl)glycine.

Starting from 1-bromonaphthalen-2-ylsulfonyl chloride, the objective compound was obtained in a manner similar to Step 1 of Example 1.

Melting point: 199.7–204.1° C.
NMR (DMSO-d$_6$, ppm): 3.77 (2H, d, J=6.0 Hz), 7.49–8.47 (7H, m)

Step 2

Preparation of 1-(1-bromonaphthalen-2-ylsulfonyl)-2-thiohydantoin.

Starting from the product obtained in Step 1, the objective compound was obtained in a manner similar to Step 2 of Example 1.

Melting point: 253.7° C. (decomposition)
NMR (DMSO-d$_6$, ppm): 5.01 (2H, s), 7.71–8.80 (6H, m)

Step 3

Preparation of 1-(1-bromonaphthalen-2-ylsulfonyl)hydantoin.

A mixture of the product obtained in Step 2 (7.5 g) and 50% (w/v) nitric acid (50 ml) was heated with stirring on a boiling water bath for 30 minutes and 60% (w/v) nitric acid (25 ml) was added. The reaction mixture was heated with stirring on a boiling water bath for 2 hours. The resultant solution was cooled in an ice bath, and the formed precipitate was separated by filtration and washed successively with water, methyl alcohol and dichloromethane to give 2.7 g of the objective compound.

Melting point: 287.4–292.5° C.
IR (KBr, cm$^{-1}$): 3200, 1740, 1370, 1180
NMR (DMSO-d$_6$, ppm): 4.78 (2H, s), 7.79–8.52 (6H, m), 11.75 (1H, s)

EXAMPLE 3

Preparation of 1-(3,6-dichloronaphthalen-2-ylsulfonyl)hydantoin (compound 7).

Step 1

Preparation of N-(3,6-dichloronaphthalen-2-ylsulfonyl)glycine.

To a solution of potassium carbonate (11.7 g) and glycine (6.4 g) in water (140 ml) were added 3,6-dichloronaphthalen-2-ylsulfonyl chloride (20.8 g) and dioxane (50 ml) at room temperature, and the mixture was stirred under reflux for 2 hours. After cooling to room temperature, the resultant solution was acidified with 2 N hydrochloric acid to a pH in the range of 1 to 2, and extracted with ethyl acetate. The organic layer was washed with water, then with saturated aqueous NaCl solution, and dried over anhydrous sodium sulfate. Ethyl acetate was removed in vacuo to give 19.0 g of the objective compound.

Melting point: 185.0–188.2° C.
NMR (DMSO-d$_6$, ppm): 3.82 (2H, d, J=8.0 Hz), 7.49–8.34 (5H, m), 8.63 (1H, s)

Step 2

Preparation of 1-(3,6-dichloronaphthalen-2-ylsulfonyl)-2-thiohydantoin

Starting from the product obtained in Step 1, the objective compound was obtained in a manner similar to Step 2 of Example 1.

Melting point: 252.8° C. (decomposition)
NMR (DMSO-d$_6$, ppm): 4.92 (2H, s), 7.38–8.32 (4H, m), 8.90 (1H, s)

Step 3

Preparation of 1-(3,6-dichloronaphthalen-2-ylsulfonyl)hydantoin.

Starting from the product obtained in Step 2, the objective compound was obtained in a manner similar to Step 3 of Example 1.

Melting point: 263.1–266.5° C.
IR (KBr, cm$^{-1}$): 3220, 1740, 1355, 1170
NMR (DMSO-d$_6$, ppm): 4.67 (2H, s), 7.74 (1H, d), 8.18–8.43 (3H, m), 8.98 (1H, s), 11.77 (1H, bs)

EXAMPLE 4

Preparation of 1-(5-nitronaphthalen-2-ylsulfonyl)hydantoin (compound 11).

Step 1

Preparation of N-(5-nitronaphthalen-2-ylsulfonyl)glycine.

To a solution of potassium carbonate (3.2 g) and glycine (1.7 g) in water (50 ml) was added 5-nitronaphthalen-2-ylsulfonyl chloride (5 g) at room temperature, and the mixture was stirred under reflux for 5 minutes. After cooling to room temperature, the resultant solution was acidified with 2 N hydrochloric acid to a pH in the range of 1 to 2, and the formed precipitate was separated by filtration to give 5.4 g of the objective compound.

Melting point: 235.7–240.7° C.
IR (KBr, cm$^{-1}$): 3353, 1718, 1519, 1335, 1143
NMR (DMSO-d., ppm): 3.70 (2H, d, J=5.9 Hz), 7.73–8.64 (7H, m), 12.60 (1H, bs)

Step 2

Preparation of 1-(5-nitronaphthalen-2-ylsulfonyl)-2-thiohydantoin.

Starting from the product obtained in Step 1, the objective compound was obtained in a manner similar to Step 2 of Example 1.

Melting point: 249.6–254.8° C.
IR (KBr, cm$^{-1}$): 3303, 1794, 1767, 1519, 1453, 1343, 1163
NMR (DMSO-d$_6$, ppm): 4.88 (2H, s), 7.80–9.03 (6H, m), 12.67 (1H, bs)

Step 3

Preparation of 1-(5-nitronaphthalen-2-ylsulfonyl)hydantoin.

Starting from the product obtained in Step 2, the objective compound was obtained in a manner similar to Step 3 of Example 1.

Melting point: 241.6–245.6° C.
IR (KBr, cm$^{-1}$): 3265, 1801, 1737, 1523, 1340
NMR (DMSO-d$_6$, ppm): 4.58 (2H, s), 7.81–8.96 (6H, m), 11.64 (1H, bs)

EXAMPLE 5

Preparation of 1-(6-acetamidonaphthalen-2-ylsulfonyl)hydantoin.

Step 1

Preparation of N-(6-acetamidonaphthalen-2-ylsulfonyl)glycine.

Starting from 6-acetamidonaphthalen-2-ylsulfonyl chloride, the objective compound was obtained in a manner similar to Step 1 of Example 1.

Melting point 202.2–204.0° C.
NMR (DMSO-d$_6$, ppm): 2.11 (3H, s), 3.36 (2H, s), 5.01 (1H, bs), 7.58–8.40
(7H, m), 10.38 (1H, bs)

Step 2

Preparation of 1-(6-acetamidonaphthalen-2-ylsulfonyl)-2-thiohydantoin.

Starting from the product obtained in Step 1, the objective compound was obtained in a manner similar to Step 2 of Example 1.

Melting point: 274.0–276.9° C.
NMR (DMSO-d$_6$, ppm): 2.13 (3H, s), 4.85 (2H, s), 7.74–8.65 (6H, m), 10.30
(1H, s), 12.60 (1H, bs)

Step 3

Preparation of 1-(6-acetamidonaphthalen-2-ylsulfonyl)hydantoin.

To a mixture of the product obtained in Step 2 (1.45 g), sodium bicarbonate (16 g), carbon tetrachloride (40 ml) and water (120 ml) was added slowly a solution of iodine monochloride (6.9 ml) in 1 N hydrochloric acid 40 ml) at room temperature. After stirring at room temperature for 10 minutes, 6 N hydrochloric acid (320 ml) was added, and the resultant solution was extracted with ethyl acetate. The organic layer was washed with saturated aqueous sodium sulfite solution, then with saturated aqueous NaCl solution, and dried over anhydrous sodium sulfate. Ethyl acetate was removed in vacuo, and the residue was washed with dichloromethane to give 1.0 g of the objective compound.

Melting point: >300° C.
IR (KBr, cm$^{-1}$): 3400, 3250, 1740, 1360, 1165
NMR (DMSO-d , ppm): 2.14 (3H, s), 4.55 (2H, s), 7.60–8.56 (6H, m), 10.49
(1H, s), 11.60 (1H, s)

Compounds of Example 6 to 25 prepared in a manner similar to Example 1 are summarized in the following table 3 together with corresponding IR and NMR data and melting points.

TABLE 3

Q—SO$_2$—N⟨hydantoin ring⟩

| Ex. No. | Q | IR(KBr, cm$^{-1}$) | NMR(DMSO-d$_6$, ppm) | M.P. (°C.) |
|---|---|---|---|---|
| 6 | 3-Cl-naphthalen-2-yl | 3250, 1735, 1350, 1160 | 4.57(2H, s), 7.67~8.34(5H, m), 8.74(1H, s), 11.60(1H, bs) | 259.6~262.0 |
| 7 | 1-Cl-naphthalen-2-yl | 3250, 1735, 1350, 1165 | 4.58(2H, s), 7.89~8.73(6H, m), 11.62(1H, bs) | 256.7~261.0 |
| 8 | 8-Cl-naphthalen-2-yl | 3230, 1730, 1350, 1160 | 4.57(2H, s), 7.62~8.80(6H, m), 11.62(1H, bs) | 293.0~299.5 |
| 9 | 6-Cl-naphthalen-2-yl | 3230, 1720, 1350, 1150 | 4.57(2H, s), 7.69~8.75(6H, m), 11.61(1H, bs) | 238.7~241.4 |
| 10 | 7-Cl-naphthalen-2-yl | 3160, 1730, 1375, 1170 | 4.56(2H, s), 7.71~8.70(6H, m), 11.62(1H, bs) | 261.0~263.9 |

TABLE 3-continued

Q—SO$_2$—N(—CH$_2$—C(=O)—)(—C(=O)—NH—) (hydantoin structure)

| Ex. No. | Q | IR(KBr, cm$^{-1}$) | NMR(DMSO-d$_6$, ppm) | M.P. (°C.) |
|---|---|---|---|---|
| 11 | 1-chloro-naphthalen-yl | 3230, 1730, 1350, 1160 | 4.56(2H, s), 7.69~8.82(6H, m), 11.61(1H, bs) | 233.7~235.3 |
| 12 | 3-bromo-naphthalen-2-yl | 3240, 1730, 1360, 1180 | 4.72(2H, s), 7.74~8.26(4H, m), 8.54(1H, s), 8.96(1H, s), 11.77(1H, bs) | 298.0~303.0 |
| 13 | 6-bromo-naphthalen-2-yl | 3220, 1730, 1350, 1160 | 4.57(2H, s), 7.80~8.74(6H, m), 11.61(1H, bs) | 255.6~258.6 |
| 14 | nitro-methyl-naphthalenyl | 3250, 1735, 1520, 1340, 1150 | 3.08(3H, s), 4.58(2H, s), 7.90~8.73(5H, m), 11.69(1H, bs) | 232.0~236.5 |
| 15 | 2,3-dimethyl-naphthalen-yl | 3200, 1725, 1340, 1160 | 2.70(3H, s), 4.55(2H, s), 7.62~8.14(5H, m), 8.75(1H, s), 11.65(1H, bs) | 271.4~277.3 |
| 16 | 1-nitro-2-methyl-naphthalen-yl | 3170, 1730, 1530, 1370, 1170 | 2.52(3H, s), 4.55(2H, s), 7.74~8.48(4H, m), 8.85(1H, s), 11.62(1H, bs) | 295.0~296.1 |
| 17 | 7-methyl-naphthalen-2-yl | 3240, 1735, 1350, 1160 | 2.53(3H, s), 4.56(2H, s), 7.51~8.63(6H, m), 11.58(1H, bs) | 212.1~215.3 |
| 18 | 1-nitro-2-methoxy-naphthalen-yl | 3180, 1740, 1530, 1370, 1170 | 4.11(3H, s), 4.54(2H, s), 7.75~8.83(5H, m), 11.61(1H, bs) | 285.9~286.4 |
| 19 | 1-fluoro-naphthalen-2-yl | 3170, 1720, 1365, 1180 | 4.56(2H, s), 7.78~8.20(6H, m), 11.67(1H, bs) | 231.0~234.0 |
| 20 | 6-fluoro-naphthalen-2-yl | 3230, 1730, 1350, 1150 | 4.50(2H, s), 7.78~8.39(6H, m), 11.60(1H, bs) | 1.62.6~166.0 |

TABLE 3-continued $$Q-SO_2-N\underset{O}{\overset{O}{\diagdown}}\hspace{-1em}\diagup\overset{O}{\diagdown}NH$$

| Ex. No. | Q | IR(KBr, cm$^{-1}$) | NMR(DMSO-d$_6$, ppm) | M.P. (°C.) |
|---|---|---|---|---|
| 21 | H$_3$CO–, H$_3$CO–, NO$_2$– naphthyl | 3250, 1735, 1365, 1165 | 4.02(3H, s), 4.06(3H, s), 4.54(2H, s), 7.72~8.80(4H, m), 11.65(1H, bs) | 228.0~230.0 |
| 22 | Br–, NC– naphthyl | 3150, 2230, 1735, 1380, 1170 | 4.57(2H, s), 8.01~8.91(5H, m), 11.65(1H, bs) | 279.0~185.0 |
| 23 | CN– naphthyl | 3230, 2240, 1740, 1380, 1160 | 4.58(2H, s), 7.93~8.49(4H, m), 8.75(1H, s), 8.84(1H, s), 11.63(1H, bs) | 261.6~264.6 |
| 24 | Cl, Cl, Cl, Cl– naphthyl | 3230, 1740, 1380, 1170 | 4.54(2H, s), 8.27~8.87(3H, m), 11.60(1H, bs) | >300 |
| 25 | H$_3$C, H$_3$C–N– naphthyl | 3240, 1740, 1370, 1170 | 2.94(6H, s), 4.53(2H, s), 7.35~8.59(6H, m), 11.56(1H, bs) | 102.9~104.5 |

EXAMPLE 26

Preparation of 1-(benzo[b]thiophen-2-ylsulfonyl)-hydantoin (compound 16).

Step 1

Preparation of benzo[b]thiophen-2-ylsulfonyl chloride.

To a solution of benzo[b]thiophen (38.3 g) in anhydrous ether (180 ml) was added dropwise 1.6 M solution of n-butyllithium in hexane (220 ml) under ice-cooling and nitrogen atmosphere. After refluxing for 40 minutes, into the solution was bubbled sulfur dioxide for 2.75 hours with stirring at −30° C. Then the solution was stirred, for 1 hour and the formed precipitate was separated by filtration to give lithium benzo[b]thiophen-2-ylsulfinate. Into the suspension of the product in concentrated hydrochloric acid (400 ml) and water (100 ml) was bubbled chlorine gas for 1.5 hours with stirring at -5° C. The resulting solution was poured into ice-water (500 ml) and extracted with dichloromethane (1.5 l ×2) and the organic layer was washed with saturated aqueous NaCl solution. After drying over anhydrous magnesium sulfate, dichloromethane was removed in vacuo, and the residue was purified by silica gel column chromatography to give 40.4 g of the objective compound.

IR (KBr, cm$^{-1}$): 1495, 1384, 1189, 1168, 1155
NMR (CDCl$_3$, ppm): 7.49–7.68 (2H, m),
7.86–8.03 (2H, m),
8.14 (1H, s)

Step 2

Preparation of N-(benzo[b]thiophen-2-ylsulfonyl)glycine.

Starting from benzo[b]thiophen-2-ylsulfonyl chloride, the objective compound was obtained in a manner similar to Step 1 of Example 1.

Melting point: 171.3–172.4° C.
IR (KBr, cm$^{-1}$): 3267, 1735, 1352, 1258, 1115, 1115
NMR (DMSO-d$_6$, ppm): 3.73 (2H, d, J=6.0 Hz),
7.39–7.61 (2H, m), 7.77–8.13
(3H, m), 8.51 (1H, d,
J=6.0 Hz), 12.68 (1H, bs)

Step 3

Preparation of 1-(benzo[b]thiophen-2-ylsulfonyl)-2-thiohydantoin.

Starting from the product obtained in Step 2, the objective compound was obtained in a manner similar to Step 2 of Example 1.

Melting point: 218.6° C. (decomposition)
IR (KBr, cm$^{-1}$): 1759, 1374, 1255, 1171, 1157
NMR (DMSO-d$_6$, ppm): 4.74 (2H, s), 7.35–7.69
(2H, m), 8.04–8.21 (2H, m),
8.45 (1H, s), 12.72 (1H, bs)

Step 4

Preparation of 1-(benzo[b]thiophen-2-ylsulfonyl)-hydantoin.

To a suspension of iodine monochloride (7.12 ml) in 1 N hydrochloric acid (200 ml) were added successively the product obtained in Step 3 (8.50 g) and dichloromethane (200 ml). The mixture was stirred for 20 minutes at room temperature. After adding sodium bicarbonate (6.85 g), the reaction mixture was stirred for 15 minutes and extracted twice with ethyl acetate (1 l +300 ml). The organic layer was washed with saturated aqueous sodium bisulfite solution and then saturated aqueous NaCl solution, and dried over anhydrous magnesium sulfate. Ethyl acetate was removed in vacuo, the residue was washed with dichloromethane to give 4.83 g of the objective compound.

Melting point: 251.8–254 2° C.
IR (KBr, cm$^{-1}$): 3245, 1803, 1740, 1376, 1352, 1167
NMR (DMSO-d$_6$, ppm): 4.48 (2H, s), 7.51–7.63 (2H, m), 8.05–8.20 (2H, m), 8.33 (1H, s), 11.71 (1H, bs)

EXAMPLE 27

Preparation of 1-(benzo[b]furan-2-ylsulfonyl)hydantoin (compound 19).

Step 1
Preparation of benzo[b]furan-2-ylsulfonyl chloride.

Starting from benzo[b]furan, the objective compound was obtained in a manner similar to Step 1 of Example 26.

IR (KBr, cm$^{-1}$): 1533, 1389, 1244, 1193, 1166
NMR (CDCl$_3$, ppm): 7.32–7.82 (5H, m)

Step 2
Preparation of N-(benzo[b]furan-2-ylsulfonyl)glycine.

Starting from benzo[b]furan-2-ylsulfonyl chloride, the objective compound was obtained in a manner similar to Step 1 of Example 1.

Melting point: 177.0–178.2° C.
NMR (DMSO-d$_6$, ppm): 3.77 (2H, d, J=6.3 Hz), 7.35–7.81 (5H, m), 8.72 (1H, t, J=6.3 Hz), 12.69 (1H, bs)

Step 3
Preparation of 1-(benzo[b]furan-2-ylsulfonyl)-2-thiohydantoin.

To a suspension of the product obtained in Step 2 (37.0 g) and ammonium thiocyanate (24. 3 g) in acetic anhydride (100 ml) was added dropwise anhydrous pyridine (30.5 ml), and the mixture was heated with stirring for 1.5 hours at 70–80° C. After cooling to room temperature, the resultant solution was poured into ice (800 g), and the formed precipitate was separated by decantation. The precipitate was washed with water and dried to give 18.5 g of the objective compound.

Melting point: 213.0° C. (decomposition)
IR (KBr cm$^{-1}$): 3080 1759 1386 1255 1167 1086
NMR (DMSO-d$_6$, ppm): 4.76 (2H, s), 7.34–8.04 (5H, m), 12.81 (1H, bs)

Step 4
Preparation of 1-(benzo[b]furan-2-ylsulfonyl) hydantoin.

Starting from the product obtained in Step 3, the objective compound was obtained in a manner similar to Step 4 of Example 26.

Melting point: 255.9–256.4° C.
IR (KBr, cm$^{-1}$): 1803, 1735, 1398, 1360, 1166
NMR (DMSO-d$_6$, ppm): 4.49 (2H, s), 7.33–8.08 (5H, m), 11.79 (1H, bs)

Compounds of Example 28 to 52 prepared in a manner similar to Example 26 are summarized in the following table 4 together with corresponding IR and NMR data and melting points.

TABLE 4

Q—SO$_2$—N(CH$_2$C(=O)NHC(=O))

| Ex. No. | Q | IR(KBr, cm$^{-1}$) | NMR(DMSO-d$_6$, ppm) | M.P. (°C.) |
|---|---|---|---|---|
| 28 | naphthyl with NO$_2$ | 1803, 1755, 1516, 1372, 1350, 1165 | 4.55(2H, s), 7.86~9.10(6H, m), 11.62(1H, bs) | 284.6 (dec.) |
| 29 | F-benzo[b]thiophen-2-yl | 1735, 1508, 1382, 1167 | 4.47(2H, s), 7.40~8.30(3H, m), 8.30(1H, s), 11.73(1H, bs) | 275.2 (dec.) |
| 30 | Cl-benzo[b]thiophen-2-yl | 1739, 1380, 1192 | 4.45(2H, s), 7.57~7.69(1H, m), 8.15~8.25(2H, m), 8.29(1H, s), 11.70(1H, bs) | >300 |
| 31 | 3-Cl-benzo[b]thiophen-2-yl | 1728, 1381, 1183, 1162 | 4.64(2H, s), 7.58~7.81(2H, m), 7.96~8.06(1H, m), 8.18~8.29(1H, m), 11.82(1H, bs) | 278.3 (dec.) |

TABLE 4-continued

Q—SO$_2$—N(CH$_2$CO)(CONH) [hydantoin-like structure]

| Ex. No. | Q | IR(KBr, cm$^{-1}$) | NMR(DMSO-d$_6$, ppm) | M.P. (°C.) |
|---|---|---|---|---|
| 32 | 4-chloro-2-methylbenzo[b]thiophene | 3270, 1741, 1379, 1162 | 4.51(2H, s), 7.52~7.67(2H, m), 8.16~8.23(2H, m), 11.74(1H, bs) | 271.1~272.2 |
| 33 | 5-bromo-2-methylbenzofuran | 3400, 1730, 1663, 1614, 1380, 1169 | 3.96(2H, s), 7.61~8.06(4H, m) | 270.2 (dec.) |
| 34 | 5-chloro-2-methylbenzofuran | 3379, 1616, 1608, 1381, 1233, 1166 | 3.98(2H, s), 7.47~7.90(4H, m) | 290.0 (dec.) |
| 35 | 2,6-dimethylbenzothiazole | 1740, 1376, 1166 | 2.88(3H, s), 4.53(2H, s), 8.10(2H, s), 8.80(1H, s), 11.59(1H, bs) | 258.0 (dec.) |
| 36 | 2-methylbenzimidazole | 3328, 1740, 1390, 1159 | 4.60(2H, s), 7.33~7.78(5H, m), 11.85(1H, bs) | 222.8 (dec.) |
| 37 | 3-methylbenzo[b]thiophene | 1741, 1380, 1162 | 4.54(2H, s), 7.52~7.63(2H, m), 8.10~8.29(2H, m), 8.86(1H, s), 11.58(1H, bs) | 218.3~226.7 |
| 38 | 3-methylbenzisothiazole | 1739, 1377, 1165 | 4.49(2H, s), 7.50~8.28(4H, m), 11.68(1H, bs) | 237.8~243.0 |
| 39 | 2-acetyl-7-methoxy-5-methylbenzofuran (—COCH$_3$) | 1746, 1682, 1363, 1158 | 2.59(3H, s), 4.07(3H, s), 4.51(2H, s), 7.57~8.13(3H, m), 11.55(1H, bs) | 263.0 (dec.) |
| 40 | 2-acetyl-7-methoxy-4-methylbenzofuran (—COCH$_3$) | 1735, 1691, 1387, 1173 | 2.63(3H, s), 4.10(3H, s), 4.54(2H, s), 7.36(1H, d, J=8.6Hz), 8.02(2H, m), 11.56(1H, bs) | 242.3~244.1 |
| 41 | 6-methylcoumarin | 1803, 1746, 1716, 1377, 1164 | 4.51(2H, s), 6.64(1H, d, J=9.9Hz), 7.62(1H, d, J=8.9Hz), 8.11~8.46(3H, m), 11.60(1H, bs) | 262.8~267.8 |

TABLE 4-continued

Q—SO$_2$—N(CH$_2$C(=O))C(=O)NH (hydantoin structure)

| Ex. No. | Q | IR(KBr, cm$^{-1}$) | NMR(DMSO-d$_6$, ppm) | M.P. (°C.) |
|---|---|---|---|---|
| 42 | 2-methyl-benzothiazol-5-yl (with CH$_3$) | 1741, 1371, 1169 | 2.87(3H, s), 4.55(2H, s), 7.95~8.51(3H, m), 11.59(1H, bs) | 245.2~246.3 |
| 43 | 1H-benzotriazol-5-yl | 1741, 1362, 1168 | 4.55(2H, s), 8.12(2H, s), 8.82(1H, s), 12.67(1H, bs) | |
| 44 | benzo[d]isoxazol-5-yl | 3098, 1743, 1385, 1364, 1186, 1162, 1067 | 4.52(2H, s), 7.99~8.66(3H, m), 9.45(1H, d, J=1.0Hz), 11.59(1H, bs) | 203 (dec.) |
| 45 | benzo[b]thiophen-4-yl | 3095, 1741, 1373, 1360, 1177, 1150 | 4.56(2H, s), 7.51~8.51(5H, m), 11.59(1H, bs) | 238.7~244.9 |
| 46 | benzo[b]thiophen-5-yl | 1729, 1362, 1166 | 4.54(2H, s), 7.66~8.59(5H, m), 11.56(1H, bs) | 268.4~271.4 |
| 47 | benzo[b]thiophen-7-yl | 3174, 1735, 1390, 1170 | 4.61(2H, s), 7.57~7.74(2H, m), 7.95~8.34(3H, m), 11.55(1H, bs) | 242.9~244.3 |
| 48 | furan-2-yl | 1800, 1742, 1396, 1162 | 4.43(2H, s), 6.78(1H, m), 7.45(1H, d, J=3.6Hz), 8.09(1H, m), 11.72(1H, bs) | 243.0~244.2 |
| 49 | 2,5-dichloro-3-methyl-thiophen-4-yl | 3227, 1735, 1365, 1183, 1171 | 4.51(2H, s), 7.55(1H, s), 11.76(1H, bs) | 251.2~251.3 |
| 50 | pyridin-3-yl | 1742, 1375, 1174 | 4.53(2H, s), 7.71(1H, m), 8.40(1H, m), 8.89~9.14(2H, m), 11.65(1H, bs) | 175.5 (dec.) |
| 51 | CH$_3$— | 1744, 1384, 1359, 1164, 1153 | 3.35(3H, s), 4.33(2H, s), 11.65(1H, bs) | 196.2~198.3 |
| 52 | biphenyl-4-yl | 1749, 1727, 1371, 1170 | 4.55(2H, s), 7.38~8.16(9H, m), 11.63(1H, bs) | 261.0~261.5 |

EXAMPLE 53

Preparation of 1-(4,5-diphenylthiophen-2-ylsulfonyl)-hydantoin.

Step 1

Preparation of 4,5-diphenylthiophen-2-ylsulfonyl chloride.

Starting from 2,3-diphenylthiophen, the objective compound was obtained in a manner similar to Step 1 of Example 26.

IR (KBr, cm$^{-1}$): 1382, 1172, 1038, 698, 583
NMR (CDCl$_3$, ppm): 7.27–7.33 (10H, m), 7.89 (1 H, s)

Step 2

Preparation of N-(4,5-diphenylthiophen-2-ylsulfonyl)glycine ethyl ester.

To a suspension of 4,5-diphenylthiophen-2-ylsulfonyl chloride (36.5 g) and glycine ethyl ester hydrochloride (30.4 g) in dichloromethane (320 ml) was added slowly triethylamine (3.03 ml) under ice-cooling, and the mixture was stirred for 160 minutes at room temperature. Water (200 ml) was added to the resultant solution, and extracted with dichloromethane. The organic layer was washed successively with 1 N hydrochloric acid, water and saturated aqueous NaCl solution, and dried over anhydrous magnesium sulfate. Dichloromethane was removed in vacuo, and the residue was reprecipitated from ethyl acetate and hexane to give 41.1 g of the objective compound.

Melting point: 151.2–152.7° C.
IR (KBr, cm$^{-1}$): 3266, 1734, 1354, 1231, 1215, 1164, 1127
NMR (DMSO-d$_6$, ppm): 1.12 (3H, t, J=7.1 Hz),
3.88 (2H, d, J=6.3 Hz),
4.04 (2H, q, J=7.1 Hz),
6.84–7.44 (10H, m), 7.67
(1H, s), 8.57 (1H, t, J=6.3 Hz)

Step 3

Preparation of N-(4,5-diphenylthiophen-2-ylsulfonyl)glycine.

A solution of sodium hydroxide (12.4 g) in water (73 ml) was added to a solution of the product obtained in Step 2 (41.4 g) in tetrahydrofuran (730 ml), and the mixture was stirred for 25 minutes at 60° C. After removing the solvent, water (300 ml) was added to the residue, and the resultant solution was acidified with concentrated hydrochloric acid to a pH 1 under ice-cooling. The acidified solution was extracted thrice with ethyl acetate (800 ml), the organic layer was washed with water, then with saturated aqueous NaCl solution, and dried over anhydrous sodium sulfate. Ethyl acetate was removed in vacuo, the residue was reprecipitated from ethyl acetate and hexane to give 37.6 g of the objective compound.

Melting point: 172.2–174.4° C.
IR (KBr, cm$^{-1}$): 3268, 1736, 1353, 1159
NMR (DMSO-d$_6$, ppm): 3.78 (2H, d, J=5.9 Hz),
7.12–7.42 (10H, m), 7.67
(1H, s), 8.39 (1H, t, J=5.9
Hz), 12.78 (1H, bs)

Step 4

Preparation of 1-(4,5-diphenylthiophen-2-ylsulfonyl)-2-thiohydantoin.

Starting from the product obtained in Step 3, the objective compound was obtained in a manner similar to Step 2 of Example 1.

Melting point: 213.2–215.4° C.
IR (KBr, cm$^{-1}$): 1752, 1446, 1376, 1168, 1083
NMR (DMSO-d$_6$, ppm): 4.77 (2H, s), 7.32–7.46
(10H, m), 8.12 (1H, s), 12.73
(1H, bs)

Step 5

Preparation of 1-(4,5-diphenylthiophen-2-ylsulfonyl)-hydantoin.

Starting from the product obtained in Step 4, the objective compound was obtained in a manner similar to Step 4 of Example 26.

Melting point: 242.5–243.9° C.
IR (KBr, cm$^{-1}$): 1737, 1386, 1165
NMR (DMSO-d$_6$, ppm): 4.53 (2H, s)
(10H, m), 8.00 (1H, s), 11.72
(1H, bs)

Compounds of Example 54 and 55 prepared in a manner similar to Example 53 are summarized in the following table 5 together with corresponding IR and NMR data and melting points.

TABLE 5

Q—SO$_2$—N(CH$_2$)C(=O)NHC(=O) [hydantoin structure]

| Ex. No. | Q | IR(KBr, cm$^{-1}$) | NMR (DMSO-d$_6$, ppm) | M.P. (°C.) |
|---|---|---|---|---|
| 54 | cyclohexylmethyl | 1721, 1367, 1349, 1172, 1161 | 0.96~2.40(10H, m), 3.30~3.69(1H, m) 4.31(2H, s), 11.61(1H, bs) | 154.9~156.7 |
| 55 | H$_3$C(CH$_2$)$_n$— | 1735, 1725, 1359, 1163 | 0.69~1.98(15H, m), 3.42~3.59(2H, m) 4.33(2H, s), 11.64(1H, bs) | 141.3~143.2 |

EXAMPLE 56

Preparation of 1-(5-nitrobenzo[b]thiophen-2-ylsulfonyl)hydantoin. (compound 42).

Step 1

Preparation of 5-nitrobenzo[b]thiophen-2-ylsulfonyl chloride.

To a solution of 5-nitrobenzo[b]thiophen (60 g) in anhydrous tetrahydrofuran (2 l) was added dropwise a solution of lithium diisopropylamide comprising 1.6 M n-butyllithium in hexane (240 ml) and diisopropylamine (57.8 ml) and anhydrous ether (170 ml) with stirring at −70° C. under nitrogen atmosphere. After stirring for 30 minutes, into the solution was bubbled sulfur dioxide for 90 minutes with stirring at −70° C. Then the solution was stirred for 1 hour at room temperature and the formed precipitate was separated by filtration to give lithium 5-nitrobenzo[b]thiophen-2-ylsulfinate. Into the suspension of the product in concentrated hydrochloric acid (500 ml) and water (125 ml) was bubbled chlorine gas for 3 hours with sufficiently stirring at below 0° C. After stirring for 1 hour at room temperature, the resulting suspension was extracted with dichloromethane (400 ml ×2) and the organic layer was washed with successive water and saturated aqueous NaCl solution. After drying over anhydrous sodium sulfate, dichloromethane was removed in vacuo, and the residue was purified by silica gel column chromatography to give 21 g of the objective compound.

IR (KBr, cm$^{-1}$): 1602, 1519, 1378, 1340, 1172
NMR (CDCL$_3$, ppm): 8.10 (1H, d, J=8.9 Hz),
8.31 (1H, s),
8.46 (1H, dd, J=8.9, 2.0 Hz),
8.90 (1H, d, J=2.0 Hz)

Step 2

Preparation of N-(5-nitrobenzo[b]thiophen-2-ylsulfonyl)glycine.

Starting from 5-nitrobenzo[b]thiophen-2-ylsulfonyl chloride, the objective compound was obtained in a manner similar to Step 1 of Example 1.

Melting point: 187.2–194.8° C.
IR (KBr, cm$^{-1}$): 3325, 1734, 1530, 1377, 1351, 1159
NMR (DMSO-d$_6$, ppm): 3.76 (2H, d, J=5.9 Hz),
8.22 (1H, s), 8.32–8.91
(4H, m), 12.72 (1H, bs)

Step 3

Preparation of 1-(5-nitrobenzo[b]thiophen-2-ylsulfonyl)-2-thiohydantoin.

Starting from the product obtained in Step 2, the objective compound was obtained in a manner similar to Step 2 of Example 1.

Melting point: 217.4° C. (decomposition)
IR (KBr, cm$^{-1}$): 1762, 1521, 1470, 1389, 1347, 1248, 1173, 1087
NMR (DMSO-d$_6$, ppm): 4.73 (2H, s), 8.25–9.09
(4H, m), 12.78 (1H, bs)

Step 4

Preparation of 1-(5-nitrobenzo[b]thiophen-2-ylsulfonyl)hydantoin.

A mixture of the product obtained in Step 3 (1.66 g) and 50% (w/v) nitric acid (35 ml) was heated with stirring for 6 hours at 60° C., and the resultant solution was poured into ice-water (150 ml). The formed precipitate was separated by fitration and washed with acetone to give 0.47 g of the objective compound.

Melting point: 282.4° C. (decomposition)
IR (KBr, cm$^{-1}$): 3100, 1737, 1522, 1385, 1349 1176
NMR (DMSO-d$_6$, ppm): 4.47 (2H, s), 8.22–9.05
(4H, m), 11.70 (1H, bs)

EXAMPLE 57

Preparation of 1-(5-cyanobenzo[b]thiophen-2-ylsulfonyl)hydantoin.

Step 1

Preparation of 5-cyanobenzo[b]thiophen-2-ylsulfonyl chloride.

Starting from benzo[b]thiophen-5-ylcarbonitrile, the objective compound was obtained in a manner similar to Step 1 of Example 56.

IR (KBr, cm$^{-1}$): 2236, 1500, 1376, 1171, 577
NMR (DMSO-d$_6$, ppm): 7.56 (1H, s), 7.70 (1H, dd, J=8.9, 2.0 Hz),
8.15 (1H, d, J=8.9 Hz ),
8.37 (1H, d, J=2.0 Hz )

Step 2

Preparation of N-(5-cyanobenzo[b]thiophen-2-ylsulfonyl)glycine.

Starting from 5-cyanobenzo[b]thiophen-2-ylsulfonyl chloride, the objective compound was obtained in a manner similar to Step 1 of Example 1.

IR (KBr, cm$^{-1}$): 3289, 2235, 1714, 1350, 1153
NMR (DMSO-d , ppm): 3.75 (2H, d, J=5.6 Hz),
7.87 (1H, dd, J=8.6, 1.3
Hz), 8.06 (1H, s), 8.34 (1H,
d, J=8.6 Hz), 8.56 (1H, d,
J=1.3 Hz), 8.70 (1H, t, J=
5.6 Hz), 12.69 (1H, bs)

Step 3

Preparation of 1-(5-cyanobenzo[b]thiophen-2-ylsulfonyl)-2-thiohydantoin.

Starting from the product obtained in Step 2, the objective compound was obtained in a manner similar to Step 2 of Example 1.

IR (KBr, cm$^{-1}$): 2231, 1762, 1451, 1243, 1173, 1077
NMR (DMSO-d$_6$, ppm): 4.73 (2H, s), 7.95 (1H, dd, J=8.6, 1.7 Hz), 8.41 (1H,
d, J=8.6 Hz), 8.53 (1H, s),
8.63 (1H, d, J=1.7 Hz),
12.72 (1H, bs)

Preparation of 1-(5-cyanobenzo[b]thiophen-2-ylsulfonyl)hydantoin.

A mixture of the product obtained in Step 3 (0.39 g) and 50% (w/v) nitric acid (8.2 ml) was heated with stirring for 5 minutes at 80° C., then for 30 minutes at room temperature, and the resultant solution was poured into ice-water (35 ml). The formed precipitate was separated by filtration and washed with acetone (100 ml) to give 0.11 g of the objective compound.

Melting point: 276.3° C. (decomposition)
IR (KBr, cm$^{-1}$): 3100, 2231, 1740, 1386, 1172
NMR (DMSO-d$_6$, ppm): 4.47 (2H, s), 7.95 (1H, dd, J=8.6, 1.7 Hz), 8.41 (1H, s),
8.42 (1H, d, J=8.6 Hz),
8.65 (1H, d, J=1.7 Hz),
11.75(1H, bs)

EXAMPLE 58

Preparation of 1-(5-carboxybenzo[b]thiophen-2-ylsulfonyl)hydantoin.

To the suspension of the product obtained in Step 4 of Example 57 (0.1 g) in water (1.5 ml) was added slowly concentrated sulfuric acid (1.5 ml) and acetic acid (1.5 ml) under ice-cooling, and the mixture was stirred under reflux for 2 hours. After cooling to room temperature, the formed precipitate was separated by filtration and washed with acetone (20 ml). The washings were concentrated in vacuo, and the residue was triturated with ether (2 ml) to give 0.02 g of the objective compound.

Melting point: >300° C.
IR (KBr, cm$^{-1}$): 1743, 1690, 1380, 1163
NMR (DMSO-d$_6$, ppm): 4.46 (2H, s), 8.07 (1H, dd, J=8.6, 1.7 Hz), 8.28 (1H,
d, J=8.6 Hz), 8.48 (1H, s),
8.69(1H, d, J=1.7 Hz)

EXAMPLE 59

Preparation of 1-(indol-2-ylsulfonyl)hydantoin.
Step 1

Preparation of 1-benzenesulfonylindol-2-ylsulfonyl chloride.

To a solution of lithium diisopropylamide comprising 1.6 M n-butyllithium in hexane (422 ml), diisopropylamine (101 ml) and anhydrous ether (260 ml) was added dropwise a solution of 1-benzenesulfonylindole (150 g) in anhydorous ether (2060 ml) with stirring at 0° C. After stirring for 15 minutes at 0° C., the solution was poured into sulfuryl chloride (125 ml) at −50° C. and stirred for 2 hours. The resulting solution was poured into ice-water (2.5 l) and stirred sufficiently and then the organic layer was extracted. The aqueous layer was extracted with ethyl acetate (2 l) and the combined organic layer was washed with successive water and saturated aqueous NaCl solution. After drying over anhydrous sodium sulfate, ether and ethyl acetate were removed in vacuo and the residue was triturated with ether to give 146 g of the objective compound.

IR (KBr, cm$^{-1}$): 1513, 1387, 1378, 1245, 1188
NMR (CDCl$_3$, ppm): 7.29–8.36 (10H, m)

Step 2

Preparation of N-(1-benzenesulfonylindol-2-ylsulfonyl)glycine ethyl ester.

Starting from 1-benzenesulfonylindol-2-ylsulfonyl chloride, the objective compound was obtained in a manner similar to Step 2 of Example 53.

IR (KBr, cm$^{-1}$): 3335, 1746, 1346, 1338, 1171
NMR (DMSO-d$_6$, ppm): 1.11 (3H, t, J=7.3 Hz),
3.94 (2H, d, J=5.6 Hz),
4.06 (2H, q, J=7.3 Hz),
6.38 (1H, t, J=5.6 Hz),
7.14–8.32 (10H, m)

Step 3

Preparation of N-(indol-2-ylsulfonyl)glycine.

A solution of sodium hydroxide (1.6 g) in water (7 ml) was added to a solution of the product obtained in Step 2 (4.22 g) in tetrahydrofuran (70 ml) at room temperature, and the mixture was stirred for 5 minutes at 65–75° C. After removing tetrahydofuran in vacuo, a solution of sodium hydroxide (0.4 g) in water (23 ml) was added to the residue, and the mixture was stirred for 5 hours at 65–75° C. After cooling to room temperature, the resultant solution was washed with ether, acidified with 6 N hydrochloric acid to a pH 1 under ice-cooling, and extracted with ethyl acetate (15 ml 3). The organic layer was washed with water and saturated aqueous NaCl solution, and dried over anhydrous sodium sulfate. Ethyl acetate was removed in vacuo, and the residue was triturated with ethyl acetate and hexane to give 1.66 g of the objective compound.

Melting point: 170.2–171.9° C.
IR (KBr, cm$^{-1}$): 3328, 1707, 1340, 1155, 1145
NMR (DMSO-d$_6$, ppm): 3.73 (2H, d, J=6.3 Hz),
6.94–7.70 (5H, m), 8.05
(1H, t, J=6.3 Hz), 11.90
(1H, bs), 12.67 (1H, bs)

Step 4

Preparation of 1-(indol-2-ylsulfonyl)-2-thiohydantoin.

Starting from the product obtained in Step 3, the objective compound was obtained in a manner similar to Step 2 of Example 1.

Melting point: 209.2–210.4° C.
IR (KBr, cm$^{-1}$): 3131, 3103, 1755, 1473, 1367, 1249, 1197, 1165, 1147, 1079
NMR (DMSO-d$_6$, ppm): 4.81 (2H, s), 7.08–7.78 (5H, m), 12.33 (1H, bs),
12.66 (1H, bs)

Step 5

Preparation of 1-(indol-2-ylsulfonyl)hydantoin.

Starting from the product obtained in Step 4, the objective compound was obtained in a manner similar to Step 4 of Example 26.

Melting point: 287.1° C. (decomposition)
IR (KBr, cm$^{-1}$): 3290, 1787, 1725, 1389, 1365, 1156
NMR (DMSO-d$_6$, ppm): 4.67 (2H, s), 7.29–7.58
(5H, m), 11.67 (1H, bs),
12.63 (1H, bs)

EXAMPLE 60

Preparation of 1-(2-carboxychromon-6-ylsulfonyl)hydantoin.

Step 1

Preparation of 2-methoxycarbonylchromon-6-ylsulfonyl chloride.

To a solution of methyl 6-aminochromon-2-carboxylate (20 g) in water (132 ml) was added concentrated sulfuric acid (26.4 ml) and then sodium nitrite (9.0 g) at 0° C. After stirring for 30 minutes, to the solution was added sulfur dioxide (19.7 ml), acetic acid (112 ml), concentrated hydrochloric acid (26 ml) and copper (II) chloride dihydrate (11.2 g) and then the mixture was stirred for 15 minutes. The formed precipitate was separated by filtration and dissolved in dichloromethane (600 ml) and the resulting solution was washed with saturated aqueous NaCl solution. After drying over anhydrous sodium sulfate, dichloromethane was removed in vacuo to give 22 g of the objective compound.

IR (KBr, cm$^{-1}$): 1744, 1661, 1381, 1287, 1174, 600
NMR (DMSO-d$_6$, ppm): 6.96 (1H, s),
7.70 (1H, d, J=8.6 Hz),
8.04 (1H, dd, J=8.6, 2.0
Hz), 8.25 (1H, d, J=2.0 Hz)

Step 2

Preparation of N-(2-methoxycarbonylchromon-6-ylsulfonyl)glycine.

To a suspension of 2-methoxycarbonylchromon-6-ylsulfonyl chloride (20.0 g) in acetone (600 ml) was added slowly a solution of glycine (6.15 g), sodium hydroxide (3.28 g) and sodium bicarbonate (6.11 g) in water (300 ml), and the mixture was stirred for 85 minutes at room temperature. After adjusting a pH of the resultant solution to ca. 6 with 6 N hydochloric acid, acetone was removed in vacuo, and insoluble matters were filtered off. The filtrate was acidified with 2 N hydrochloric acid to a pH 1 under ice-cooling. The acidified solution was extracted with ethyl acetate (350 ml 3), the organic layer was washed with water, then saturated aqueous NaCl solution, and dried over anhydrous sodium sulfate. Ethyl acetate was removed in vacuo, the residue was purified by silica-gel column chromatography to give 5.45 g of the objective compound.

Melting point: 210.6–212.8° C.
IR (KBr, cm$^{-1}$): 3327, 1746, 1716, 1659, 1288, 1266, 1165
NMR (DMSO-d$_6$, ppm): 3.67 (2H, d, J=5.9 Hz),
3.96 (3H, s), 7.04 (1H, s),
7.89–8.42 (4H, m)

Step 3

Preparation of 1-(2-methoxycarbonylchromon-6-ylsulfonyl)-2-thiohydantoin.

Starting from the product obtained in Step 2, the objective compound was obtained in a manner similar to Step 2 of Example 1.

Melting point: 217.4° C. (decomposition)
IR (KBr, cm$^{-1}$): 1746, 1660, 1443, 1374, 1282, 1260, 1174
NMR (DMSO-d$_6$, ppm): 3.96 (3H, s), 4.84 (2H, s), 7.07 (1H, s), 7.97–8.71 (3H, m), 12.68 (1H, bs)

Step 4

Preparation of 1-(2-methoxycarbonylchromon-6-ylsulfonyl)hydantoin.

Starting from the product obtained in Step 3, the objective compound was obtained in a manner similar to Step 4 of Example 26.

Melting point: >300° C.
IR (KBr, cm$^{-1}$): 1751, 1741, 1664, 1617, 1375, 1177,
NMR (DMSO-d$_6$, ppm): 3.96 (3H, s), 4.52 (2H, s) 7.07 (1H, s), 7.98–8.64 (3H, m)

Step 5

Preparation of 1-(2-carboxychromon-6-ylsulfonyl)hydantoin.

A solution of the product obtained in Step 4 (2.27 g) in a saturated aqueous sodium bicarbonate solution (22.7 ml) was stirred for 2 hours at 40° C. The resultant solution was washed with ethyl acetate and acidified with 2 N hydrochloric acid to a pH 1 under ice-cooling, and the formed precipitate was separated by filtration to give 0.82 g of the objective compound.

Melting point: 279.3° C. (decomposition)
IR (KBr, cm$^{-1}$): 3220, 1751, 1663, 1376, 1172
NMR (DMSO-d$_6$, ppm): 4.54 (2H, s), 7.02 (1H, s), 7.95–8.61 (3H, m), 11.63 (1H, bs)

EXAMPLE 61

Preparation of 1-(benzothiazol-2-ylsulfonyl)hydantoin (compound 22).

Step 1

Preparation of 2-benzylthiobenzothiazole.

To a solution of 2-benzothiazolthiol (250 g) in N,N-dimethylformamide (1 l) was added triethylamine (208 ml) under ice-cooling and dropwise a solution of benzyl bromide (178 ml) in N,N-dimethylformamide (300 ml) and the mixture was stirred for 40 minutes. The resulting solution was poured into water (10 l) and the formed precipitate was separated by filtration and dissolved in dichloromethane (3 l). After drying over anhydorpus magnesium sulfate, dichloromethane was removed in vacuo to give 378 g of the objective compound.

Step 2

Preparation of benzothiazol-2-ylsulfonyl chloride.

Into a mixture of 2-benzylthiobenzothiazole (100 g) and acetic acid (500 ml) in water (500 ml) was bubbled chlorine gas for 1.5 hours with stirring at −15° C. The resulting solution was poured into ice-water (1.5 l), the formed precipitate was separated by filtration to give 90.9 g of the objective compound.

Step 3

Preparation of N-(benzothiazol-2-ylsulfonyl)glycinamide.

To a suspension of glycinamide hydrochloride (43 g) in dioxane (1 l) was added benzothiazol-2-ylsulfonyl chloride (90.9 g) under ice-cooling, and a pH of the mixture was adjusted to 8 with saturated aqueous sodium carbonate solution. After stirring for 1.5 hours, the resultant solution was concentrated in vacuo. Water (1.5 l) was added to the residue, and the solution was acidified with concentrated hydrochloric acid to pH 2. The formed precipitate was separated by filtration to give 59.8 g of the objective compound.

Melting point: 179.7–181.8° C.
IR (KBr, cm$^{-1}$): 3426, 1682, 1346, 1165
NMR (DMSO-d$_6$, ppm): 3.73 (2H, s), 7.08 (1H, bs), 7.36 (1H, bs), 7.52–8.29 (4H, m), 8.80 (1H, bs)

Step 4

Preparation of N-(benzothiazol-2-ylsulfonyl)N-methoxycarbonylglycinamide.

To a solution of the product obtained in Step 3 (102.3 g) in N,N-dimethylformamide (1.2 l) was added slowly 60% sodium hydride (16.7 g) under ice-cooling, and the mixture was stirred for 1 hour at room temperature. Methyl chlorocarbonate (35.8 g) was added to the above-mentioned mixture followed by stirring for 1 hour at room temperature. After removing the solvent, water (3.5 l) was added to the residue, and the formed precipitate was separated by filtration to give 60.5 g of the objective compound.

Melting point: 153.1° C. (decomposition)
IR (KBr, cm$^{-1}$): 3459, 3346, 1737, 1689, 1386, 1343, 1250, 1171
NMR (DMSO-d$_6$, ppm): 3.70 (3H, s), 4.51 (2H, s), 7.30 (1H, bs), 7.60–7.76 (3H, m), 8.20–8.39 (2H, m)

Step 5

Preparation of 1-(benzothiazol-2-ylsulfonyl)hydantoin.

To a solution of the product obtained in Step 4 (20.0 g) in N,N-dimethylformamide (200 ml) added slowly 60% sodium hydride (2.67 g), and the mixture was stirred for 13.5 hours at 70° C. After removing the solvent, water (1 l) was added to the residue, and the solution was extracted with ethyl acetate (1.5 l). The organic layer was washed with saturated aqueous NaCl solution, and dried over anhydrous sodium sulfate. Ethyl acetate was removed in vacuo, and the residue was washed with acetone-chloroform (100 ml + 200 ml) to give 2.12 g of the objective compound.

Melting point: 260.4–261 9° C.
IR (KBr, cm$^{-1}$): 3200, 3105, 1739, 1393, 1355, 1173
NMR (DMSO-d$_6$, ppm): 4.55 (2H, s), 7.61–7.81 (2H, m), 8.18–8.40 (2H, m), 11.88 (1H, bs)

EXAMPLE 62

Preparation of 1-(benzo[c]thiophen-1-ylsulfonyl)hydantoin.

Step 1

Preparation of N$^2$-(benzo[c]thiophen-1-ylsulfonyl)glycinamide.

To a solution of benzo[c]thiophen (5.5 g) in anhydrous ether (50 ml) was added 1.6 M solution of nbutyllithium in hexane (52.2 ml) at −20° C. under nitrogen atmosphere. After stirring for 1 hour, into the solution was bubbled sulfur dioxide for 1 hour with stirring at −20° C. Ether was removed in vacuo and the residue was suspended in isopropanol (200 ml) and water (200 ml). To the suspension was added N-chlorosuccinimide (6.5 g) at 0° C. After stirring for 30 minutes at 0° C., N-chlorosuccinimide (1.63 g) was added and the mixture was stirred for additional 1 hour. The resulting solution was extracted with dichloromethane (1 l×2) and the organic layer was washed with successive water and saturated aqueous NaCl solution. After drying over anhydrous sodium sulfate, dichloromethane was removed in vacuo under cooling. Using this residue and glycinamide hydrochloride, the objective compound was obtained in a manner similar to Step 3 of Example 50.

NMR (DMSO-d6, ppm): 3.40 (2H, d, J=6.9 Hz), 7.06-8.22 (5H, m), 8.49 (1H, s)

Step 2

Preparation of N-(benzo[c]thiophen-1-ylsulfonyl)N²-methoxycarbonylglycinamide.

To a solution of the product obtained in Step 1 (0.45 g) in N,N-dimethylformamide (5 ml) was added slowly 60% sodium hydride (75 mg) under ice-cooling, and the mixture was stirred for 30 minutes at room temperature. Methyl chloroformate (0.14 ml) was added to the above-mentioned mixture followed by stirring for 20 minutes at room temperature. 60% sodium hydride (75 mg) was added to the solution, and the mixture was stirred for 1.5 hours at room temperature, then 15 minutes at 70° C. After cooling to room temperature, water (20 ml) was added to the resultant mixture and this aqueous solution was extracted with ethyl acetate (20 ml×3). The organic layer was washed with water, then saturated aqueous NaCl solution. After drying over anhydrous magnesium sulfate, ethyl acetate was removed in vacuo and the residue was purified by silica-gel columun chromatography to give 0.18 g of the objective compound.

NMR (CDCl₃, ppm): 3.74 (3H, s), 4.24 (2H, d, J=5.3 Hz), 5.92 (1H, t, J=5.3 Hz), 7.17-8.31 (6H, m)

Step 3

Preparation of 1-(benzo[c]thiophen-1-ylsulfonyl)-hydantoin.

To a solution of the product obtained in Step 2 (0.18 g) in N,N-dimethylformamide (3 ml) added slowly 60% sodium hydride (48 mg), and the mixture was stirred for 2.5 hours at 70° C. After removing the solvent, ice water (20 ml) was added to the residue, and pH of the solution was adjusted to 4 with 1 N hydrochloric acid. The resultant solution was extracted with ethyl acetate (20 ml×3), and the organic layer was washed with saturated aqueous NaCl solution, and dried over anhydrous magnesium sulfate. Ethyl acetate was removed in vacuo, and the residue was triturated with dichloromethane to give 0.03 g of the objective compound.

Melting point: 223.6–226.9° C.

IR (KBr, cm⁻¹): 1736, 1378, 1185, 1162, 1152

NMR (DMSO-d6, ppm): 4.51 (2H, s), 7.20–8.16 (4H, m), 8.82 (1H, s), 11.54 (1H, bs)

Intermediate compounds of Example 6 to 25, 28 to 52, 54 and 55 are summarized to the following table 6 and 7 together with corresponding IR and NMR data and melting points.

TABLE 6

| Ex. No. | Q | Q—SO₂NHCH₂CO₂H IR(KBr, cm⁻¹) | NMR (DMSO-d6, ppm) | M.P. (°C.) |
|---|---|---|---|---|
| 6 | 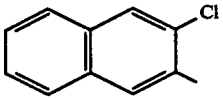 | 3345, 1710, 1315, 1140 | 3.69(2H, d), 7.61~8.37(6H, m), 8.49(1H, s) | 174.5~182.1 |
| 7 | 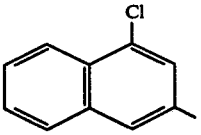 | | 3.70(2H, d, J=5.9Hz), 7.72~8.50(7H, m) | 185.2~186.4 |
| 8 | 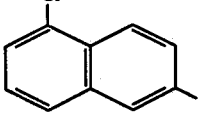 | | 3.44(2H, s), 7.52~8.60(7H, m) | >300 |
| 9 | 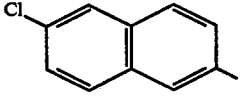 | 3350, 1715, 1320, 1145 | 3.55(2H, d, J=5.8Hz), 7.51~8.30(6H, m), 8.48(1H, s) | 158.8~165.7 |
| 10 | 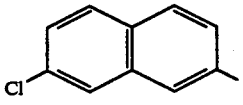 | | 3.73(2H, s), 7.51~8.53(7H, m) | 247.8~254.7 |
| 11 | 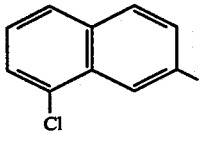 | | 3.69(2H, d, J=6.0Hz), 7.58~8.71(7H, m) | 157.8~162.1 |
| 12 | 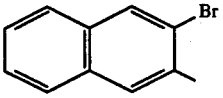 | 3345, 1715, 1330, 1165 | 3.78(2H, d, J=5.9Hz), 7.61~8.22(5H, m), 8.42(1H, s), 8.64(1H, s) | 210.0~214.4 |

TABLE 6-continued
| Ex. No. | Q | Q—SO₂NHCH₂CO₂H IR(KBr, cm⁻¹) | NMR (DMSO-d₆, ppm) | M.P. (°C.) |
|---|---|---|---|---|
| 13 | 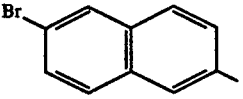 | 3350, 1715, 1320, 1145 | 3.48(2H, s), 7.52~8.48(7H, m) | 257.2~265.7 |
| 14 | 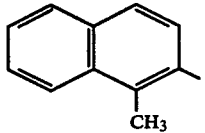 | | 2.98(3H, s), 3.62(2H, d, J=5.9Hz), 7.52~8.35(7H, m) | 179.0~182.7 |
| 15 | 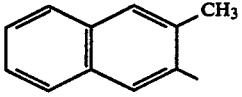 | | 2.79(3H, s), 3.73(2H, d, J=6.1Hz), 7.43~8.35(6H, m), 8.53(1H, s) | 155.5~160.5 |
| 16 | 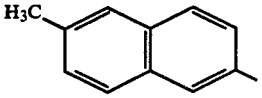 | | 2.49(3H, s), 3.40(2H, s), 7.35~8.39(7H, m) | 225.7~230.6 |
| 17 | 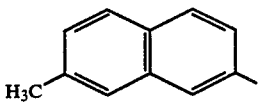 | | 2.49(3H, s), 3.65(2H, s), 7.35~8.45(7H, m) | 147.4~152.0 |
| 18 | 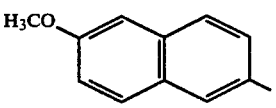 | 3340, 1710, 1325, 1155 | 3.62(2H, d, J=6.0Hz), 3.91(3H, s), 7.19~8.15(6H, m), 8.31(1H, s) | 161.4~163.6 |
| 19 | 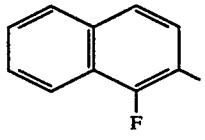 | | 3.78(2H, d, J=5.9Hz), 7.67~8.45(7H, m) | 163.5~168.5 |
| 20 | 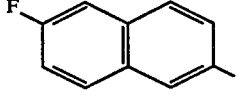 | | 3.62(2H, s), 7.05~8.50(7H, m) | 109.0~109.5 |
| 21 | 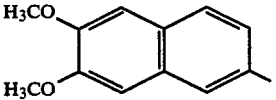 | | 3.55(2H, s), 3.93(6H, s), 7.35~7.98(5H, m), 8.24(1H, s) | 212.6~217.1 |
| 22 | 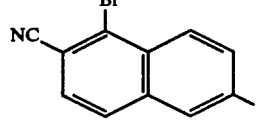 | 3280, 2230 1760, 1155 | 3.71(2H, d, J=6.0Hz), 7.87~8.65(6H, m) | 231.9~234.9 |
| 23 | 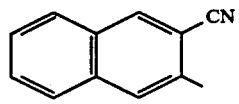 | 3260, 2240, 1740, 1155 | 3.69(2H, d, J=6.0Hz), 7.82~8.73(7H, m) | 186.2~192.0 |
| 24 | 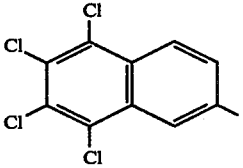 | | 3.72(2H, d, J=5.7Hz), 8.09~8.68(4H, m) | 258.8~261.5 |

TABLE 6-continued
Q—SO₂NHCH₂CO₂H
| Ex. No. | Q | IR(KBr, cm⁻¹) | NMR (DMSO-d₆, ppm) | M.P. (°C.) |
|---|---|---|---|---|
| 25 | 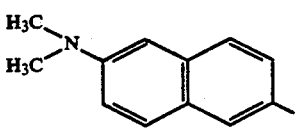 | | 3.06(6H, s), 3.55(2H, d, J=60Hz), 6.91~8.21(7H, m) | 148.0~152.0 |
| 28 | 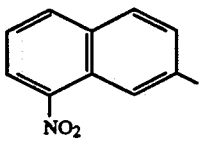 | 3348, 1710, 1518, 1334, 1142 | 3.68(2H, d, J=6.3Hz), 7.78~8.89(7H, m) 12.63(1H, bs) | 224.9~227.7 |
| 29 | 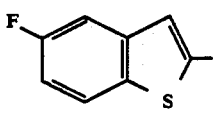 | 3290, 1709, 1342, 1156 | 3.73(2H, d, J=5.9Hz), 7.31~8.22(4H, m), 8.59(1H, t, J=5.9Hz), 12.72(1H, bs) | 162.7~164.2 |
| 30 | 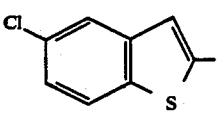 | 3295, 1709, 1343, 1156 | 3.73(2H, d, J=5.9Hz), 7.49~8.17(4H, m), 8.59(1H, t, J=5.9Hz), 12.54(1H, bs) | 186.9~189.1 |
| 31 | 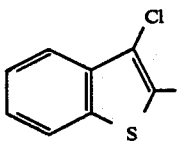 | 3337, 1716, 1342, 1257, 1162 | 3.83(2H, d, J=6.3Hz), 7.52~8.24(4H, m), 8.87(1H, t, J=6.3Hz), 12.63(1H, bs) | 156.6~161.0 |
| 32 | 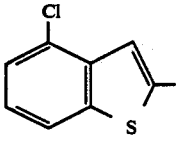 | 3255, 1710, 1356, 1248, 1160 | 3.78(2H, d, J=5.9Hz), 7.44~8.13(4H, m), 8.66(1H, t, J=5.9Hz), 12.68(1H, bs) | 197.0~199.2 |
| 33 | 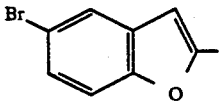 | 3334, 1717, 1437, 1352, 1241, 1152 | 3.78(2H, s), 7.49(1H, s), 7.68(2H, s), 8.00(1H, s), 8.83(1H, bs) | 192.4~194.1 |
| 34 | 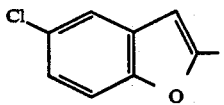 | 3377, 1718, 1358, 1247, 1157 | 3.76(2H, s) 7.44~7.89(4H, m) | 191.5~193.8 |
| 35 | 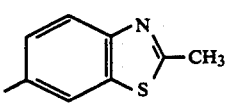 | 3290, 1720, 1340, 1170 | 2.86(3H, s), 3.63(2H, d, J=6.3Hz), 7.79~8.54(4H, m), 12.48(1H, bs) | 237.7 (dec.) |
| 36 | 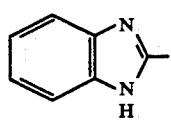 | 3068, 1718, 1617, 1349, 1155 | 3.78(2H, s), 7.25~7.70(4H, m) | 133.5~135.9 |
| 37 | 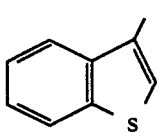 | 3318, 1724, 1339, 1241, 1152 | 3.64(2H, d, J=5.9Hz), 7.36~7.60(2H, m), 7.97~8.45(4H, m) | |

TABLE 6-continued
Q—SO₂NHCH₂CO₂H
| Ex. No. | Q | IR(KBr, cm⁻¹) | NMR (DMSO-$d_6$, ppm) | M.P. (°C.) |
|---|---|---|---|---|
| 38 | 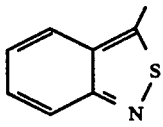 | 3094, 1721, 1348, 1164 | 3.82(2H, s), 7.43~8.17(4H, m), 9.09(1H, bs), 12.51(1H, bs) | 212.5~214.4 |
| 39 | 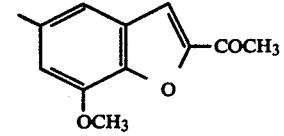 | 3290, 1733, 1655, 1331, 1158 | 2.58(3H, s), 3.61(2H, d, J=5.9Hz), 4.03(3H, s), 7.49~8.17(4H, m), 12.50(1H, bs) | 215.0~217.6 |
| 41 | 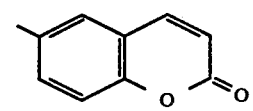 | 3265, 1748, 1711, 1316, 1205, 1154 | 3.65(2H, d, J=5.9Hz), 6.62(1H, d, J=9.9Hz), 7.57(1H, d, J=8.6Hz), 7.92~8.25(4H, m), 12.69(1H, bs) | 235.0 (dec.) |
| 42 | 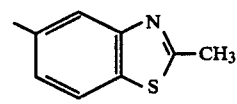 | 3302, 1727, 1330, 1216, 1154 | 2.85(3H, s), 3.63(2H, d, J=5.9Hz), 7.73~8.29(4H, m) | 257.2 (dec.) |
| 43 | 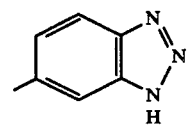 | 3213, 1718, 1317, 1255, 1164, 1153 | 3.64(2H, d, J=5.6Hz), 7.78~8.38(4H, m) | 243.5~245.3 |
| 44 | 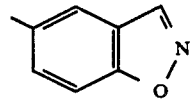 | 3271, 1742, 1316, 1149 | 3.64(2H, d, J=6.3Hz), 7.90~8.63(4H, m), 9.38(1H, s), 12.57(1H, bs) | 165.3~168.5 |
| 45 | 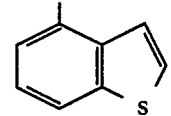 | 3097, 1741, 1316, 1209, 1148 | 3.57(2H, d, J=5.9Hz), 7.39~8.33(6H, m) | |
| 46 | 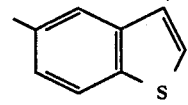 | 3186, 1765, 1751, 1732, 1335, 1145 | 3.60(2H, d, J=6.3Hz), 7.61~8.35(6H, m), 12.58(1H, bs) | |
| 47 | 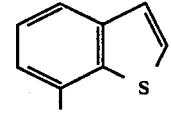 | 3282, 1727, 1309, 1161, 1137 | 3.65(2H, d, J=5.9Hz), 7.47~8.18(5H, m), 8.33(1H, t, J=5.9Hz), 12.64(1H, bs) | |
| 48 | 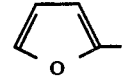 | 3307, 1725, 1340, 1329, 1157 | 3.66(2H, d, J=6.3Hz), 6.58~7.90(3H, m), 8.38(1H, t, J=6.3Hz), 12.63(1H, bs) | |
| 49 | 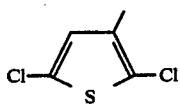 | 3358, 1728, 1348, 1236, 1166 | 3.76(2H, d, J=5.9Hz), 7.28(1H, s), 8.45(1H, t, J=5.9Hz), 12.76(1H, bs) | |
| 50 | 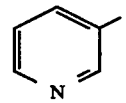 | 3236, 1701, 1341, 1174 | 3.70(2H, d, J=5.9Hz), 7.54~8.24(2H, m), 8.33(1H, t, J=5.9Hz) 8.76~8.96(2H, m), 12.70(1H, bs) | 220.4~223.8 |
| 51 | CH₃— | 3258, 1711, | 2.92(3H, s), | 168.0~171.0 |

TABLE 6-continued

Q—SO₂NHCH₂CO₂H

| Ex. No. | Q | IR(KBr, cm⁻¹) | NMR (DMSO-d₆, ppm) | M.P. (°C.) |
|---|---|---|---|---|
|  |  | 1320, 1247, 1148 | 3.72(2H, d, J=5.9Hz), 7.39(1H, t, J=5.9Hz), 12.71(1H, bs) |  |
| 52 | 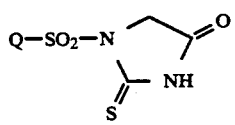 | 3348, 1714, 1323, 1152 | 3.62(2H, d, J=6.3Hz), 7.44~7.87(9H, m), 8.06(1H, t, J=6.3Hz) |  |
| 54 | (cyclohexyl-H) | 3308, 1714, 1319, 1147, 1126 | 1.18~2.06(10H, m), 2.64~3.19(1H, m), 3.69(2H, d, J=6.0Hz) 7.33(1H, t, J=6.0Hz) | 96.0~100.9 |
| 55 | H₃C—(CH₂)₇— | 3314, 3256, 2921, 1716, 1313, 1141 | 0.80~1.86(15H, m), 2.91~3.08(2H, m) 3.70(2H, d, J=5.9Hz), 7.39(1H, t, J=5.9Hz), 12.69(1H, bs) |  |

TABLE 7

Q—SO₂—N—CH₂—C(=O)—NH—C(=S) (ring)

| Ex. No. | Q | IR(KBr, cm⁻¹) | NMR(DMSO-d₆, ppm) | M.P. (°C.) |
|---|---|---|---|---|
| 6 | 2-Cl naphthyl | 3130, 1785, 1760, 1165 | 4.90(2H, s), 7.69~8.45(5H, m), 8.88(1H, s) | 212.9~222.8 |
| 7 | 1-Cl naphthyl |  | 4.88(2H, s), 7.74~8.83(6H, m) | 250.1 (dec.) |
| 8 | 1-Cl naphthyl (other isomer) |  | 4.89(2H, s), 7.59~8.43(5H, m), 8.70~8.96(1H, m) | 231.4 (dec.) |
| 9 | 6-Cl naphthyl | 3150, 1795, 1770, 1170 | 4.93(2H, s), 7.61~8.35(5H, m), 8.89(1H, s) | 211.4~221.9 |
| 10 | 7-Cl naphthyl |  | 4.88(2H, s), 7.68~8.39(5H, m), 8.80(1H, s) | 227.8 (dec.) |
| 11 | 8-Cl naphthyl |  | 4.89(2H, s), 7.60~8.29(5H, m), 8.69~8.87(1H, m) | 190.5 (dec.) |
| 12 | 2-Br naphthyl | 3270, 1795, 1770, 1170 | 4.94(2H, s), 7.65~8.51(5H, m), 8.99(1H, s) | 248.5~255.7 |

TABLE 7-continued
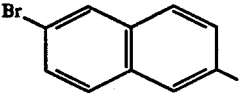
| Ex. No. | Q | IR(KBr, cm$^{-1}$) | NMR(DMSO-d$_6$, ppm) | M.P. (°C.) |
|---|---|---|---|---|
| 13 | 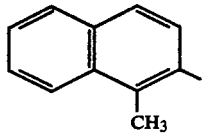 | 3120, 1785, 1755, 1165 | 4.85(2H, s), 7.70~8.40(5H, m), 8.67~8.84(1H, m) | 198.5~209.5 |
| 14 | 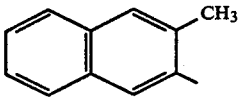 | | 2.97(3H, s), 4.86(2H, s), 7.55~8.47(6H, m) | 243.9 (dec.) |
| 15 | 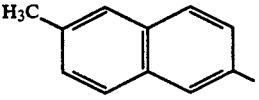 | | 2.64(3H, s), 4.80(2H, s), 7.47~8.26(5H, m), 8.81(1H, s) | 242.0~244.7 |
| 16 | 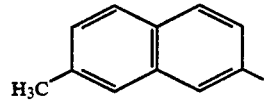 | | 2.53(3H, s), 4.91(2H, s), 7.45~8.68(5H, m), 8.70(1H, s) | 234.8~237.6 |
| 17 | 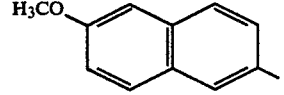 | | 2.52(3H, s), 4.71(2H, s), 7.29~8.03(5H, m), 8.58~8.69(1H, m) | 232.7~238.2 |
| 18 | 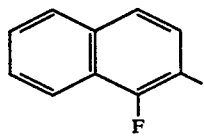 | 3250, 1790, 1755, 1165 | 3.94(3H, s), 4.85(2H, s), 7.23~7.51(2H, m), 7.87~8.17(3H, m), 8.67(1H, s) | 236.4 (dec.) |
| 19 | 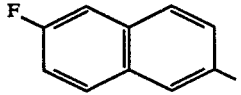 | | 4.82(2H, s), 7.67~8.33(6H, m) | 248.0 (dec.) |
| 20 | 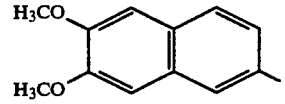 | | 4.86(2H, s), 7.23~8.61(6H, m) | 177.1~184.7 |
| 21 | 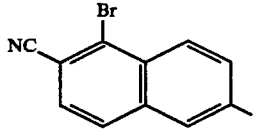 | | 3.95(6H, s), 4.86(2H, s), 7.45~7.97(4H, m), 8.45~8.59(1H, m) | 260.7 (dec.) |
| 22 | 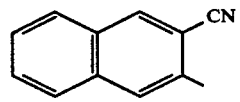 | 2230, 1760, 1350, 1170 | 4.88(2H, s), 7.88~8.55(4H, m), 8.73~9.00(1H, m) | 223.0 (dec.) |
| 23 |  | 2225, 1760, 1350, 1170 | 4.88(2H, s), 7.81~8.46(4H, m), 8.64~8.92(2H, m), 12.60(1H, bs) | 131.0~135.8 |

TABLE 7-continued
Q—SO₂—N (structure with C=O, NH, C=S)
| Ex. No. | Q | IR(KBr, cm⁻¹) | NMR(DMSO-d₆, ppm) | M.P. (°C.) |
|---|---|---|---|---|
| 24 | 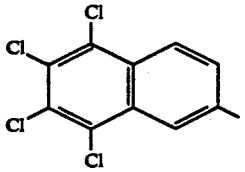 | | 4.86(2H, s), 8.46~8.99(3H, m), 12.60(1H, bs) | 270.0 (dec.) |
| 25 | 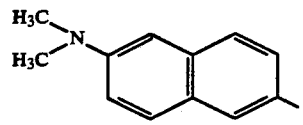 | | 3.10(6H, s), 4.82(2H, s), 6.93~8.03(5H, m), 8.47(1H, s) | 256.4 (dec.) |
| 28 | 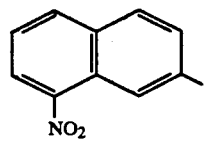 | 1793, 1764, 1527, 1345, 1172 | 4.85(2H, s), 7.80~9.24(6H, m), 12.67(1H, bs) | 229.6 (dec.) |
| 29 | 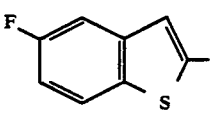 | 1757, 1391, 1253, 1176 | 4.74(2H, s), 7.41~8.50(4H, m), 12.76(1H, bs) | 240.4~242.5 |
| 30 | 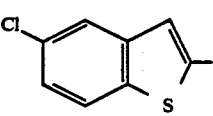 | 1761, 1468, 1385, 1249, 1170 | 4.73(2H, s), 7.50~8.46(4H, m), 12.77(1H, bs) | 208.3 (dec.) |
| 31 | 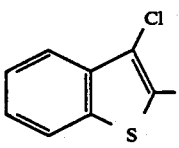 | 1784, 1756, 1462, 1374, 1245, 1173 | 4.92(2H, s), 7.50~8.34(4H, m), 12.95(1H, bs) | 275.3 (dec.) |
| 32 | 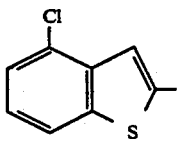 | 1746, 1467, 1382, 1257, 1171 | 4.79(2H, s), 7.53~8.40(4H, m), 12.76(1H, bs) | 221.2~224.6 |
| 33 | 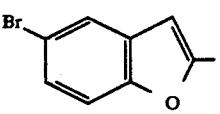 | 1751, 1436, 1392, 1237, 1165 | 4.74(2H, s), 7.65~8.10(4H, m), 12.72(1H, bs) | 186.7~187.7 |
| 34 | 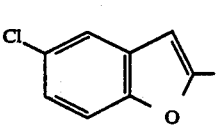 | 1750, 1458, 1394, 1164 | 4.74(2H, s), 7.50~8.07(4H, m), 12.83(1H, bs) | 213.9 (dec.) |
| 35 | 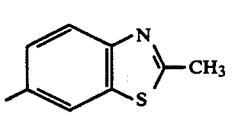 | 1748, 1378, 1245, 1175 | 2.88(3H, s), 4.83(2H, s), 8.13(2H, s), 8.87(1H, s), 12.62(1H, bs) | 240.4 (dec.) |

TABLE 7-continued

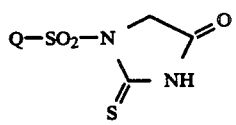

| Ex. No. | Q | IR(KBr, cm$^{-1}$) | NMR(DMSO-d$_6$, ppm) | M.P. (°C.) |
|---|---|---|---|---|
| 36 | benzimidazole-2-yl (NH, 2-methyl) | 1785, 1758, 1449, 1388, 1255, 1185, 1160 | 4.84(2H, s), 7.26~7.86(4H, m), 12.94(1H, bs) | |
| 37 | 3-methylbenzothiophen-2-yl | 3111, 1793, 1762, 1463, 1374, 1174 | 4.87(2H, s), 7.47~7.68(2H, m), 8.04~8.28(2H, m), 9.01(1H, s), 12.64(1H, bs) | |
| 38 | 3-methylbenzisothiazol-yl | 1757, 1386, 1176 | 4.83(2H, s), 7.50~8.34(4H, m), 12.77(1H, bs) | 203.1 (dec.) |
| 39 | 5-methyl-7-methoxy-2-acetylbenzofuran-yl | 1764, 1680, 1475, 1361, 1319, 1162 | 2.59(3H, s), 4.08(3H, s), 4.77(2H, s), 7.50~8.28(3H, m), 12.51(1H, bs) | 244.0 (dec.) |
| 40 | 4-methyl-7-methoxy-2-acetylbenzofuran-yl | 1746, 1671, 1362, 1305, 1186, 1167 | 2.63(3H, s), 4.10(3H, s), 4.85(2H, s), 7.32(1H, d, J=8.9Hz), 7.95(1H, s), 8.14(1H, d, J=8.9Hz), 12.54(1H, bs) | |
| 41 | 6-methylcoumarin-yl | 1745, 1467, 1385, 1360, 1170 | 4.81(2H, s), 6.65(1H, d, J=9.6Hz), 7.62(1H, d, J=8.9Hz), 8.04~8.58(3H, m), 12.66(1H, bs) | 230.2 (dec.) |
| 42 | 2-methyl-5-methylbenzothiazol-yl | 1762, 1613, 1370, 1241, 1174 | 2.87(3H, s), 4.85(2H, s), 7.92~8.64(3H, m), 12.61(1H, bs) | 226.0 (dec.) |
| 43 | 1-acetyl-6-methylbenzotriazol-yl | 1755, 1459, 1380, 1169 | 2.96(3H, s), 4.89(2H, s), 8.41(2H, s), 9.06(1H, s), 12.60(1H, bs) | 222.7 (dec.) |
| 44 | 5-methylbenzisoxazol-yl | 1759, 1459, 1370, 1243, 1189, 1162 | 4.83(2H, s), 7.99~8.75(3H, m), 9.46(1H, s), 12.64(1H, bs) | 264.0 (dec.) |
| 45 | 4-methylbenzothiophen-yl | 1745, 1476, 1362, 1267, 1199, 1170 | 4.90(2H, s), 7.46~8.55(5H, m), 12.63(1H, bs) | |

TABLE 7-continued $$Q-SO_2-N\diagdown\diagup\diagdown{}^O$$
$$\diagdown_S\diagup\diagdown NH$$

| Ex. No. | Q | IR(KBr, cm$^{-1}$) | NMR(DMSO-d$_6$, ppm) | M.P. (°C.) |
|---|---|---|---|---|
| 46 | 5-methylbenzo[b]thiophen-2-yl | 1755, 1474, 1364, 1256, 1200, 1169 | 4.84(2H, s), 7.50~8.73(5H, m), 12.58(1H, bs) | |
| 47 | benzo[b]thiophen-2-yl (7-substituted) | 1743, 1459, 1390, 1346, 1172 | 4.91(2H, s), 7.55~8.31(5H, m), 12.71(1H, bs) | |
| 48 | furan-2-yl | 1753, 1431, 1381, 1191, 1166 | 4.68(2H, s), 6.72~6.86(1H, m), 7.54(1H, d, J=3.6Hz), 8.10(1H, d, J=1.8Hz), 12.75(1H, bs) | |
| 49 | 2,5-dichloro-3-methylthiophen-4-yl | 1795, 1758, 1452, 1432, 1374, 1177 | 4.77(2H, s), 7.65(1H, s), 12.85(1H, bs) | |
| 50 | pyridin-3-yl | 1788, 1755, 1378, 1263, 1173 | 4.82(2H, s), 7.62~9.22(4H, m), 12.69(1H, bs) | 221.0 (dec.) |
| 51 | CH$_3$— | 1745, 1470, 1424, 1361, 1165 | 3.57(3H, s), 4.52(2H, s), 12.70(1H, bs) | 213.4~216.0 |
| 52 | biphenyl-4-yl | 1743, 1456, 1374, 1171 | 4.84(2H, s), 7.47~8.23(9H, m), 12.65(1H, bs) | |
| 54 | cyclohexyl | 1791, 1757, 1735, 1453, 1353, 1236, 1169 | 1.24~2.23(10H, m), 3.90~4.32(1H, m), 4.50(2H, s), 12.70(1H, bs) | |
| 55 | H$_3$C—(CH$_2$)$_n$— | 1748, 1735, 1454, 1363, 1235, 1157 | 0.54~2.04(15H, m), 3.60~4.02(2H, m), 4.51(2H, s), 12.68(1H, bs) | |

Now, typical but non-limiting examples of formulations of the compound of this invention will be shown below.

Formulation A (Capsules)

Compound 13, 300 g of weight, 685 g of lactose and 15 g of magnesium stearate were weighed and mixed until the mixture became homogeneous. The mixture was then filled in No. 1 hard gelatin capsule at 200 mg each to obtain capsule preparation.

Formulation B (Tablets)

Compound 15, 300 g of weight, 550 g of lactose, 120 g of potato starch, 15 g of polyvinyl alcohol and 15 g of magnesium stearate were weighed. The weighed amount of compound 15, lactose and potato starch were mixed until accomplishing homogeneity. Then aqueous solution of polyvinylalcohol was added to the mixture and granulated by wet process. The granules were then dried, mixed with magnesium stearate and pressed into tablets, each weighing 200 mg.

Formulation C (Powder)

Compound 8, 200 g of weight, 790 g of lactose and 10 g of magnesium stearate were weighed and mixed until the mixture became homogeneous to obtain 20% powder preparation.

Formulation D (Capsules)

Compound 16, 300 g of weight, 685 g of lactose and 15 g of magnesium stearate were weighed and mixed until the mixture became homogeneous. The mixture was then filled in No. 1 hard gelatin capsule at 200 mg each to obtain capsule preparation.

Formulation E (Tablets)

Compound 19, 300 g of weight, 550 g of lactose, 120 g of potato starch, 15 g of polyvinyl alcohol and 15 g of magnesium stearate were weighed. The weighed amount of compound 19, lactose and potato starch were mixed until accomplishing homogeneity. Then aqueous solution of polyvinylalcohol was added to the mixture and granulated by wet process. The granules were then dried, mixed with magnesium stearate and pressed into tablets, each weighing 200 mg.

Compounds of Example 63 to 77 prepared in a manner similar to Example 26 are summarized in the following table 8 together with corresponding IR and NMR data and melting points.

TABLE 8

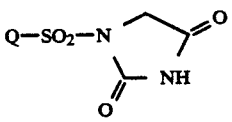

| Ex. No. | Q | IR(KBr, cm$^{-1}$) | NMR(DMSO-d$_6$, ppm) | M.P. (°C.) |
|---|---|---|---|---|
| 63 | 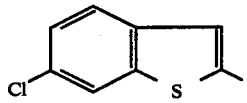 | 1800, 1750, 1739, 1381, 1160 | 4.46(2H, s), 7.57(1H, dd, J=8.6, 1.7Hz), 8.11(1H, d, J=8.6Hz), 8.33(2H, s) | 249.1~ 251.3 |
| 64 | 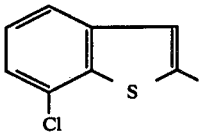 | 3096, 1786, 1734, 1376, 1166 | 4.48(2H, s), 7.50~7.81(1H, m), 8.11(1H, dd, J=6.6, 1.3Hz), 8.44(1H, s), 11.74(1H, bs) | 285.0 (dec.) |
| 65 | 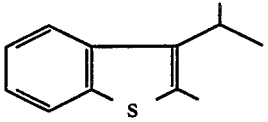 | 3210, 1809, 1728, 1392, 1160 | 1.46(6H, d, J=7.3Hz), 3.96~4.28(1H, m), 4.52(2H, s), 7.48~7.67(2H, m), 8.07~8.32(2H, m), 11.76(1H, bs) | 174.1~ 176.6 |
| 66 | 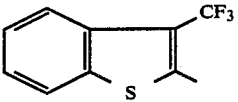 | 1733, 1379, 1180 | 4.53(2H, s), 7.66~8.38(4H, m), 11.95(1H, bs) | 243.2 (dec.) |
| 67 | 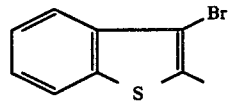 | 3160, 1805, 1725, 1379, 1183 | 4.70(2H, s), 7.57~8.28(4H, m), 11.86(1H, bs) | 288.0~ 289.5 |
| 68 | 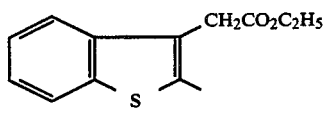 | 1804, 1744, 1378, 1178 | 1.16(3H, t, J=7.0Hz), 4.07(2H, q, J=7.0Hz), 4.42(2H, s), 4.47(2H, s), 7.53~7.66(2H, m), 7.99~8.20(2H, m), 11.73(1H, bs) | 196.0~ 197.5 |
| 69 | 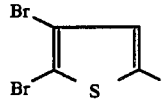 | 3300, 1779, 1729, 1382, 1173, 1167 | 4.44(2H, s), 7.95(1H, s), 11.75(1H, bs) | 283.2 (dec.) |
| 70 | 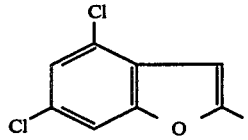 | 3270, 1807, 1742, 1389, 1169 | 4.45(2H, s), 7.72(1H, d, J=1.6Hz), 7.96(1H, d, J=1.0Hz), 8.07(1H, dd, J=1.6, 1.0Hz), 11.78(1H, bs) | 290.8 (dec.) |
| 71 | 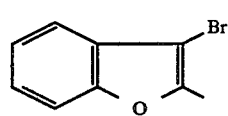 | 3220, 1800, 1783, 1397, 1176, 1154 | 4.52(2H, s), 7.43~7.91(4H, m) | 265.7~ 267.9 |

TABLE 8-continued

Q—SO₂—N group structure with NH and two C=O

| Ex. No. | Q | IR(KBr, cm⁻¹) | NMR(DMSO-d₆, ppm) | M.P. (°C.) |
|---|---|---|---|---|
| 72 | 3,4-dibromothiophene-2-yl | 3080, 1805, 1725, 1378, 1187, 1177 | 4.62(2H, s), 8.40(1H, s), 11.84(1H, bs) | 278.0 (dec.) |
| 73 | 3-bromo-7-fluorobenzothiophene-2-yl | 3209, 3177, 1812, 1726, 1490, 1379, 1305, 1176, 1162 | 4.69(2H, s), 7.51~7.90(3H, m), 11.90(1H, bs) | 286.0 (dec.) |
| 74 | 4,5,6,7-tetrahydrobenzothiophene-2-yl | 3210, 1806, 1735, 1364, 1158, | 1.62~1.92(4H, m), 2.46~2.91(4H, m), 4.40(2H, s), 7.60(1H, s), 11.61(1H, bs) | 248.3~249.5 |
| 75 | 3-phenylbenzofuran-2-yl | 1810, 1793, 1396, 1177 | 4.34(2H, s), 7.43~7.88(9H, m), 11.76(1H, bs) | 220.4 (dec.) |
| 76 | 3-fluorobenzothiophene-2-yl | 3230, 1742, 1389, 1183 | 4.47(2H, s), 7.53~8.13(4H, m), 11.72(1H, bs) | 256.0~258.0 |
| 77 | 3-fluorothiophene-2-yl | 3103, 1805, 1787, 1729, 1534, 1426, 1383, 1366, 1169 | 4.41(2H, s), 7.21(1H, d, J=5.6Hz), 8.12(1H, dd, J=5.6, 4.3Hz), 11.73(1H, bs) | 238.2~240.9 |

Compounds of Example 78 to 81 prepared in a manner similar to Example 53 are summarized in the following table 9 together with corresponding IR and NMR data and melting points.

TABLE 9

Q—SO₂—N group structure with NH and two C=O

| Ex. No. | Q | IR(KBr, cm⁻¹) | NMR(DMSO-d₆, ppm) | M.P. (°C.) |
|---|---|---|---|---|
| 78 | 3-chlorobenzothiophene-2-yl | 3170, 1787, 1732, 1365, 1171 | 4.61(2H, s), 7.50~7.61(2H, m), 8.04~8.26(2H, m), 11.72(1H, bs) | 215.0~219.0 |
| 79 | 3-nitrobenzothiophene-2-yl | 3214, 1778, 1725, 1528, 1439, 1346 | 4.53(2H, s), 7.49~7.68(2H, m), 8.03~8.17(2H, m), 11.87(1H, bs) | 221.1~223.2 |

TABLE 9-continued

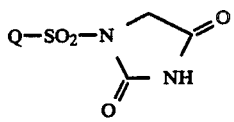

| Ex. No. | Q | IR(KBr, cm$^{-1}$) | NMR(DMSO-d$_6$, ppm) | M.P. (°C.) |
|---|---|---|---|---|
| 80 | (4-iodobenzofuran-2-yl) | 1810, 1742, 1391, 1165, 1139 | 4.48(2H, s), 7.28~7.89(4H, m), 11.61(1H, bs) | 277.0 (dec.) |
| 81 | (4-methyl-2-acetamido-thiazol-5-yl) | 3190, 3040, 1795, 1750, 1372, 1170 | 2.19(3H, s), 2.54(3H, s), 4.41(2H, s), 11.61(1H, bs), 12.73(1H, bs) | >300 |

Compounds of Example 82 and 83 prepared in a manner similar to Example 61 are summarized in the following table 10 together with corresponding IR and NMR data and melting points.

TABLE 10

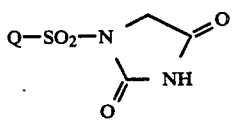

| Ex. No. | Q | IR(KBr, cm$^{-1}$) | NMR(DMSO-d$_6$, ppm) | M.P. (°C.) |
|---|---|---|---|---|
| 82 | (3-methylthiobenzo[b]thiophen-2-yl) | 3200, 1801, 1724, 1374, 1180 | 2.47(3H, s), 4.77(2H, s), 7.60~7.76(2H, m), 8.09~8.25(2H, m), 11.83(1H, bs) | 213.2~222.0 |
| 83 | (3-methoxybenzo[b]thiophen-2-yl) | 3240, 1990, 1728, 1371, 1163 | 4.18(3H, s), 4.55(2H, s), 7.55~7.66(2H, m), 8.06~8.14(2H, m), 11.70(1H, bs) | 239.7~241.3 |

EXAMPLE 84

Preparation of 1-(3-carboxymethylbenzo[b]thiophen-2-ylsulfonyl)hydantoin.

A mixture of the product obtained in Step 4 of Example 68 (0.85 g) and 60% (w/v) nitric acid (9 ml) was heated with stirring for 140 minutes at 70° C. After cooling to room temperature, the formed precipitate was separated by filtration and washed with ether to give 0.21 g of the objective compound.

Melting point: 224.4° C. (decomposition)
IR (KBr, cm$^{-1}$): 3220, 1800, 1736, 1718, 1374, 1170
NMR (DMSO-d$_6$, ppm): 4.32 (2H, s), 4.47 (2H, s), 7 55-7.65 (2H, m),
7.99-8.19 (2H, m),
11.71(1H, bs)

EXAMPLE 85

Preparation of 1-(3-methylsulfinylbenzo[b]thiophen-2-ylsulfonyl)hydantoin.

To a suspension of the product obtained in Example 82 (0.65 g) in dichloromethane (26 ml) was added mchloroperbenzoic acid (0.41 g)and the mixture wa stirred for 1.5 hours at room temperature. The resulting solution was concentrated in vacuo and the residue was washed with ether (30 ml). The residue was purified by silica gel column chromatography to give 0.48 g of the objective compound.

Melting point: 215.0–221.0° C.
NMR (DMSO-d$_6$, ppm): 3.10 (3H, s), 4.57 (2H, s), 7.51-8.89 (4H,m),
11.81 (1H, bs)

EXAMPLE 86

Preparation of 1-(3-methylsulfonylbenzo[b]thiophen-2-ylsulfonyl)hydantoin (compound 32).

To a suspension of the product obtained in Example 82 (0.65 g) in ethyl acetate (26 ml) was added m-chloroperbenzoic acid (0.82 g) and the mixture was stirred under reflux for 1.5 hours. Additional m-chloroperbenzoic acid (0.16 g) was added and the mixture was stirred under reflux for more 1.5 hours. The resulting solution was concentrated in vacuo and the residue was washed with successive methanol and ether to give 0.40 g of the objective compound.

Melting point: 224.0–245.0° C.
IR (KBr, cm$^{-1}$): 1771, 1372, 1324, 1179
NMR (DMSO-d$_6$, ppm): 3.47 (3H, s), 4.63 (2H, s), 7.66-8.59 (4H,m),
11.90(1H, bs)

EXAMPLE 87

Preparation of 1-(3-cyanobenzo[b]thiophen-2-ylsulfonyl)hydantoin (compound 33).

To a mixture of the product obtained in Example 67 (11.3 g) and copper (I) cyanide (4.1 g) was added pyridine (42 ml). After stirring at 70 °C. for 17 hours, a solution of Iron (III) chloride hexahydrate (15.7 g) in concentrated hydrochloric acid (3.9 ml) and water (23.6 ml) was added slowly to the solution and the resultant mixture was heated with stirring for 5 minutes at 50 °C. The formed precipitate was separated by filtration and the filtrate was extracted with ethyl acetate (300 ml) and the organic layer was washed with successive water and saturated aqueous NaCl solution and dried over anhydrous sodium sulfate. Above mentioned precipitate was extracted by ethanol and this ethanol solution was combined with above mentioned organic layer. The resulting solution was concentrated in vacuo and purified by silica gel column chromatography to give 1.21 g of the objective compound.

Melting point: 238.9-242.5.° C.
IR (KBr, cm$^{-1}$): 2233, 1807, 1746, 1736, 1388, 1167
NMR (DMSO-d$_6$, ppm): 4.51 (2H, s),
7.70-8.47 (4H, m),
11.83 (1H, bs)

EXAMPLE 88

Preparation of 1-(3-hydroxybenzo[b]thiophen-2-ylsulfonyl)hydantoin.

A mixture of the product obtained in Example 83 (2.5 g), acetic acid (7 ml) and 47% hydrobromic acid (8.9 ml) was stirred for 1 hour at room temperature and heated for 1 hour at 40 °C., for more 1 hour at 50° C. To the mixture was added additional acetic acid (7 ml) and 47% hydrobromic acid (8.9 ml) and heated with stirring for 1 hour at 60° C., for 2 hours at 80° C. The resulting solution was poured into water (300 ml) and extracted with ethyl acetate (1.2 l). After drying over anhydrous magnesium sulfate, ethyl acetate was removed in vacuo and the residue was dissolved in acetone (800 ml). After decoloring with activated charcoal, acetone was removed in vacuo and the residue was washed with successive ethyl acetate and ether to give 1.13 g of the objective compound.

Melting point: 171.8 °C. (decomposition)
IR (KBr, cm$^{-1}$): 3260, 1800, 1735, 1358, 1185, 1164
NMR (DMSO-d, ppm): 4.60 (2H, s),
7.46-8.19 (4H, m),
11.70 (1H, bs)

EXAMPLE 89

Preparation of 1-(3-carbamoylbenzo[b]thiophen-2-ylsulfonyl)hydantoin.

A mixture of the product obtained in Example 87 (0.84 g) and 80% (v/v) sulfuric acid (16.3 ml) was heated with stirring for 8 hours at 70° C. and the resulting solution was poured into ice-water (200 ml). The formed precipitate was separated by filtration and washed with successive water, ethanol and acetone to give 0 16 g of the objective compound.

Melting point: 241.9-244.6° C.
3197, 1795, 1741, 1376, 1162
IR (KBr, cm$^{-1}$): 3412, 3197,1795,1741, 1376, 1162
NMR (DMSO-d$_6$, ppm): 4.51 (2H, s),
7.56-8.44 (6H, m),
11.73 (1H, bs)

EXAMPLE 90

Preparation of 1-(3-carboxybenzo[b]thiophen-2-ylsulfonyl)hydantoin.

To a suspension of the product obtained in Example 89 (0.60 g) in concentrated sulfuric acid (18 ml) was added sodium nitrite (2.4 g) under cooling at −15° C. and the resulting suspension was stirred for 15 minutes at −15° C., for 30 minutes at 0° C. and for 50 minutes at room temperature. To the mixture was added additional sodium nitrite (1.2 g) and stirred for 30 minutes at room temperature. After adjusting a pH of the resulting solution to ca. 9 with 0.1 M sodium bicarbonate, the resulting solution was washed with ethyl acetate and acidified with concentrated hydrochloric acid to a pH about 2 and extracted with ethyl acetate (200 ml). The organic layer was washed with successive water and saturated aqueous NaCl solution. After drying over anhydrous sodium sulfate, ethyl acetate was removed in vacuo and the residue was purified by silica gel column chromatography to give 0.18 g of the objective compound.

Melting point: 228.8-235.1° C.
IR (KBr, cm$^{-1}$): 3450, 1739, 1735, 1380, 1175
NMR (DMSO-d$_6$, ppm): 4.73 (2H, s),
7.45-8.17 (4H, m),
11.76 (1H, bs)

EXAMPLE 91

Preparation of 1-(3-chlorobenzo[b]furan-2-ylsulfonyl)hydantoin (compound 47).
Step 1
Preparation of 3-chlorobenzo[b]furan-2-ylsulfonyl chloride.

To a solution of 3-chlorobenzo[b]furan (11.4 g) in anhydrous ether (62 ml) wa added dropwise 1.5 M lithium diisopropylamide mono(tetrahydrofuran) in hexane (62 ml) under nitrogen atmosphere at −70° C. After stirring for 30 minutes, into the solution was bubbled sulfur dioxide for 1 hour with stirring at −60° C. Then the solution was stirred for 1 hour at room temperature and the formed precipitate was separated by filtration to give lithium 3-chlorobenzo[b]furan-2-sulfinate. To the suspension of the product in dichloromethane (250 ml) was added N-chlorosuccinimide (11.0 g) at −50° C. and stirred for 3 hours. After stirring for 2 hours under ice-cooling, insoluble matters were filtered off. Dichloromethane was removed in vacuo and the residue was purified by silica gel column chromatography to give 8.8 g of the objective compound.

Melting point: 60.6-68.2° C.
IR (KBr, cm$^{-1}$): 1538, 1402, 1232, 1183, 1151, 1039
NMR (CDCl, ppm): 7.40-7.98 (4H, m)
Step 2
Preparation of N-(3-chlorobenzo[b]furan-2-ylsulfonyl)glycine ethyl ester.

To a suspension of 3-chlorobenzo[b]furan-2-ylsulfonyl chloride (8.6 g) and glycine ethyl ester hydrochloride (9.6 g) in dichloromethane (83 ml) was added slowly triethylamine (10.4 ml) under ice-cooling and then the resulting mixture was stirred for 30 minutes at room temperature. Water (150 ml) was added to the resultant solution and acidified with 1 M hydrochloric acid to a pH 2, and the acidified solution was extracted with ethyl acetate (300 ml). After drying over anhydrous magnesium sulfate, ethyl acetate was removed in vacuo to give 10.2 g of the objective compound.

Melting point: 104.5–110.8° C.
IR (KBr, cm⁻¹): 3203, 1736, 1365, 1230, 1149
NMR (DMSO-d₆, ppm): 1.01 (3H, t, J=7.1 Hz),
3.89 (2H, q, J=7.1 Hz),
3.94 (2H, s), 7.50–
7.73 (4H, m), 9.12 (1H, bs)

Step 3

Preparation of N-(3-chlorobenzo[b]furan-2-ylsulfonyl)glycine.

To a solution of N-(3-chlorobenzo[b]furan-2-ylsulfonyl)glycine ethyl ester (10.2 g) in tetrahydrofuran (160 ml) was added dropwise a solution of sodium hydroxide (4.9 g) in water (16 ml) under ice-cooling and the resulting solution was stirred for 1 hour. After stirring for 30 minutes at room temperature, tetrahydrofuran was removed in vacuo. Water (200 ml) was added to the residue and then acidified with concentrated hydrochloric acid under ice-cooling to a pH 1 and the acidified solution was extracted with ethyl acetate (500 ml). The organic layer was washed with saturated aqueous NaCl solution. After drying over anhydrous magnesium sulfate, ethyl acetate was removed in vacuo to give 9.2 g of the objective compound.

Melting point: 163.8–167.9° C.
IR (KBr, cm⁻¹): 3236, 1709, 1369, 1232, 1153
NMR (DMSO-d₆, ppm): 3.84 (2H, d, J=5.9 Hz),
7.38–7.81 (4H, m),
9.03 (1H, t, J=5.9 Hz),
12.67 (1H, bs)

Step 4

Preparation of 1-(3-chlorobenzo[b]furan-2-ylsulfonyl)-2-thiohydantoin.

To a mixture of N-(3-chlorobenzo[b]furan-2-ylsulfonyl)glycine (9.2 g), ammonium thiocyanate (5.32 g) and acetic anhydride (18 ml) was added dropwise pyridine (6.68 ml) under ice-cooling and resulting mixture was stirred for 30 minutes at room temperature, for 30 minutes at 40° C. and for 2 hours at 70–80° C. After cooling to room temperature, the resulting solution was poured into ice-water (300 ml) and the formed precipitate was separated by filtration and washed with water-ethanol to give 6.73 g of the objective compound.

Melting point: 195.4–204.7° C.
IR (KBr, cm⁻¹): 3158, 1758, 1393, 1234, 1179
NMR (DMSO-d₆, ppm): 4.83 (2H, s), 7.56–7.90 (4H, m)

Step 5

Preparation of 1-(3-chlorobenzo[b]furan-2-ylsulfonyl)hydantoin.

To a suspension of iodine monochloride (5.3 ml) in 1 M hydrochloric acid (160 ml) was added 1-(3-chlorobenzo[b]furan-2-ylsulfonyl)-2-thiohydantoin (6.7 g) and then dichloromethane (200 ml) dropwise. The mixture was stirred for 1.5 hours under ice-cooling and for 1.5 hours at room temperature. After adding saturated aqueous sodium sulfite solution, the reaction mixture was extracted with ethyl acetate (600 ml). The organic layer was washed with successive saturated aqueous sodium sulfite solution and saturated aqueous NaCl solution. After drying over anhydrous magnesium sulfate, ethyl acetate was removed in vacuo and the residue was washed with successive ether and ether-ethyl acetate to give 3.15 g of the objective compound.

Melting point: 246.6–256.8° C.
IR (KBr, cm⁻¹): 3226, 1744, 1397, 1363, 1174, 1156
NMR (DMSO-d, ppm): 4.51 (2H, s), 7.54–7.89 (4H, m), 11.81 (1H, bs)

EXAMPLE 92

Preparation of 1-(4-bromobenzo[b]furan-2-ylsulfonyl)hydantoin.

Step 1

Preparation of (3-bromophenyloxy)acetaldehyde dimethyl acetal.

To a suspension of 60% sodium hydride (60 g) in N,N-dimethylformamide (1.4 l) was added dropwise 3-bromophenol (260 g) under ice-cooling. After stirring for 10 minutes, to the solution was added dropwise bromoacetaldehyde dimethyl acetal (318 g) and the mixture was heated with stirring for 3 hours at 90° C. After cooling, water was added to the resulting solution and acidified with 1 M hydrochloric acid and then extracted with ether (3 l). The organic layer was washed with successive water, saturated aqueous sodium bicarbonate solution and saturated aqueous NaCl solution. After drying over anhydrous sodium sulfate, ether was removed in vacuo and the residue was purified by silica gel column chromatography to give 363.3 g of the objective compound.

IR (neat, cm⁻¹): 2941, 2835, 1615, 1506, 1458
NMR (CDCl₃, ppm): 3.44 (6H, s),
3.96 (2H, d, J=5.0 Hz),
4.69 (1H, t, J=5.0 Hz),
6.77–7.26 (4H, m)

Step 2

Preparation of mixture of 4-bromobenzo[b]furan and 6-bromobenzo[b]furan.

Under ice-cooling, to phosphoric acid (413.5 ml) was added phosphorus pentoxide (344.2 g) and then chlorobenzene (870 ml). The resulting mixture was heated up to 125° C. To the mixture was added dropwise the solution of the product obtained in Step 1 (181.7 g) in chlorobenzene (150 ml) at 125° C. and heated with stirring for 1 hour at 125° C. After cooling, the resulting mixture was poured into ice-water (2 l) and extracted with ether (2 l). The organic layer was washed with successive saturated aqueous sodium bicarbonate solution and saturated aqueous NaCl solution. After drying over anhydrous sodium sulfate, ether and chlorobenzene were removed in vacuo and the residue was purified by silica gel column chromatography to give 116 g of the objective compound.

Step 3

Preparation of 4-bromobenzo[b]furan-2-ylsulfonyl chloride.

To a solution of the mixture obtained in Step 2 (100 g) in anhydrous ether (430 ml) was added dropwise 1.5 M lithium diisopropylamide mono(tetrahydrofuran) in cyclohexane (430 ml) under nitrogen atmosphere at −70° C. After stirring for 30 minutes, into the solution was bubbled sulfur dioxide for 1 hour with stirring at −60° C. Then the solution was stirred for 3 hours at room temperature and the formed precipitate was separated by filtration to give a mixture of lithium 4-bromobenzo[b]furan-2-sulfinate and lithium 6-bromobenzo[b]furan-2-sulfinate. To the suspension of the products in dichloromethane (2 l) was added N-chlorosuccinimide (96 g) at −50° C. and stirred for 3 hours under ice-cooling. Insoluble matters were filtered off and dichloromethane was removed in vacuo and the residue was purified by silica gel column chromatography to give 14.1 g of the objective compound.

Melting point: 87.2° C.
cm⁻¹): 1603, 1578, 1389, 1175, 1165
IR (KBr, cm⁻¹): 1603, 1578, 1389, 1175, 1165

NMR (CDCl*, ppm): 7.43–7.67 (4H, m)

Step 4

Preparation of N-(4-bromobenzo[b]furan-2-ylsulfonyl)glycine ethyl ester.

Starting from the product obtained in Step 3 (14.1 g), the objective compound (16.8 g) was obtained in a manner similar to Step 2 of Example 91.

Melting point: 115.6–117.3° C.
IR (KBr, cm$^{-1}$): 3199, 1361, 1221, 1158
NMR (CDCl$_3$, ppm): 1.18 (3H, t, J=7.1 Hz),
3.97 (2H, d, J=5.3 Hz),
4.09 (2H, q, J=7.1 Hz),
5.45 (1H, t, J=5.3 Hz),
7 26–7.58 (4H, m)

Step 5

Preparation of N-(4-bromobenzo[b]furan-2-ylsulfonyl)glycine.

Starting from the product obtained in Step 4 (16.8 g), the objective compound (14.4 g) was obtained in a manner similar to Step 3 of Example 91.

Melting point: 180.0–182.1° C.
IR (KBr, cm$^{-1}$): 3253, 1738, 1361, 1262, 1165
NMR (DMSO-d., ppm): 3.81 (2H, s), 7.38–7.81 (4H, m), 8.85 (1H, bs)

Step 6

Preparation of 1-(4-bromobenzo[b]furan-2-ylsulfonyl)-2-thiohydantoin.

To a suspension of the product obtained in Step 5 (14.4 g) and ammonium thiocyanate (7.2 g) in acetic anhydride (28 ml) was added dropwise pyridine (9.1 ml) and the mixture was heated with stirring for 2 hours at 60–70° C.. After cooling to room temperature, the resulting solution was poured into ice-water (500 ml) and the formed precipitate was separated and washed with ethanol to give 10.7 g of the objective compound.

Melting point: 253.3° C.
IR (KBr, cm$^{-1}$): 3140, 1756, 1391, 1248, 1166
NMR (DMSO-d, ppm): 4.77 (2H, s), 7.45–7.88 (3H, m), 7.95 (1H, s),
12.86 (1H, bs)

Step 7

Preparation of 1-(4-bromobenzo[b]furan-2-ylsulfonyl)hydantoin.

Starting from the product obtained in Step 6 (10.7 g), the objective compound (4.3 g) was obtained in a manner similar to Step 5 of Example 91.

Melting point: 291.7–293.5° C.
IR (KBr, cm$^{-1}$): 3240, 1741, 1390, 1355, 1167
NMR (DMSO-d., ppm): 4.48 (2H, s), 7.45–7.90 (4H, m), 11.78 (1H, bs)

EXAMPLE 93

Preparation of 1-(7-fluorobenzo[b]furan-2-ylsulfonyl)hydantoin (compound 48).

Step 1

Preparation of 7-fluorobenzo[b]furan-2-ylsulfonyl chloride.

Starting from 7-fluorobenzo[b]furan (10.4 g), the objective compound (5.7 g) was obtained in a manner similar to Step 1 of Example 91.

Melting point: 114° C.
IR (KBr, cm$^{-1}$): 1596, 1546, 1372, 1267, 1178
NMR (CDCl$_3$, ppm): 7.24–7.69 (4H, m)

Step 2

Preparation of N-(7-fluorobenzo[b]furan-2-ylsulfonyl)glycine ethyl ester.

Starting from the product obtained in Step 1 (5.7 g), the objective compound (6.45 g) was obtained in a manner similar to Step 2 of Example 91.

Melting point: 84.5° C.
IR (KBr, cm$^{-1}$): 3238, 1734, 1376, 1232, 1165
NMR (DMSO-d$_6$, ppm): 1.03 (3H, t, J=7.1 Hz),
3.89 (2H, d, J=6.3 Hz),
3.92 (2H, q, J=7.1 Hz),
7.32–7.66 (4H, m),
9.05 (1H, t, J=6.3 Hz)

Step 3

Preparation of N-(7-fluorobenzo[b]furan-2-ylsulfonyl)glycine.

Starting from the product obtained in Step 2 (6.4 g), the objective compound (5.42 g) was obtained in a manner similar to Step 3 of Example 91.

Melting point: 140.1° C. (decomposition)
IR (KBr, cm$^{-1}$): 3303, 1734, 1349, 1262, 1160
NMR (DMSO-d$_6$, ppm): 3.80 (2H, d, J=5.0 Hz),
7.28–7.66 (4H, m),
8.90 (1H, t, J=5.0 Hz)

Step 4

Preparation of 1-(7-fluorobenzo[b]furan-2-ylsulfonyl)-2-thiohydantoin.

To a suspension of the product obtained in Step 3 (5.4 g) and ammonium thiocyanate (3.32 g) in acetic anhydride (12.7 ml) was added dropwise pyridine (4.16 ml) under ice-cooling and nitrogen atmosphere. The mixture was heated with stirring for 2 hours at 70° C. After cooling to room temperature, the resulting solution was poured into ice-water (200 ml) and added small amount of ethanol and the formed precipitate was separated and dissolved in ethyl acetate (200 ml) and the solution was washed with successive water and saturated aqueous NaCl solution. After drying over anhydrous sodium sulfate, ethyl acetate was removed in vacuo and the residue was washed with ethanol to give 2.83 g of the objective compound.

Melting point: 229.9–232.0° C.
IR (KBr, cm$^{-1}$): 3258, 1765, 1744, 1448, 1177
NMR (DMSO-d$_6$, ppm): 4.73 (2H, s), 7.39–7.77 (3H, m), 8.13 (1H, d, J=2.6 Hz), 12.83 (1H, bs)

Step 5

Preparation of 1-(7-fluorobenzo[b]furan-2-ylsulfonyl)hydantoin.

Starting from the product obtained in Step 4 (2.8 g), the objective compound (1.1 g) was obtained in a manner similar to Step 5 of Example 91.

Melting point: >300° C.
IR (KBr, cm$^{-1}$): 3381, 1735, 1610, 1383, 1166
NMR (DMSO-d$_6$, ppm): 3.98 (2H, s), 34–7.71 (3H, m), 7.78 (1H, d, J=3.0 Hz)

EXAMPLE 94

Preparation of 1-(4,5-dichlorobenzo[b]furan-2-ylsulfonyl)hydantoin (compound 44).

Step 1

Preparation of (3,4-dichlorophenyloxy)acetaldehyde dimethyl acetal.

Starting from 3,4-dichlorophenol (200 g), the objective compound (218.8 g) was obtained in a manner similar to Step 1 of Example 92.

IR (neat, cm$^{-1}$): 2940, 2830, 1595, 1475, 1297, 1235
NMR (CDCl$_3$, ppm): 3.45 (6H, s),
3.96 (2H, d, J=5.3 Hz),
4.69 (1H, t, J=5.3 Hz), 6.78 (1H, dd, J=8.9, 3.0 Hz),
7.02 (1H, d, J=3.0 Hz),
7.31 (1H, d, J=8.9 Hz)

Step 2

Preparation of mixture of 4,5-dichlorobenzo[b]furan and 5,6-dichlorobenzo[b]furan.

Starting from the product obtained in Step 1 (218.8 g), the mixture of the objective compounds (102.1 g) was obtained in a manner similar to Step 2 of Example 92.

Step 3

Preparation of 4,5-dichlorobenzo[b]furan-2-ylsulfonyl chloride and 5,6-dichlorobenzo[b]furan 2-ylsulfonyl chloride.

To a solution of the mixture obtained in Step 2 (100 g) in anhydrous ether (440 ml) was added dropwise 1.5 M lithium diisopropylamide mono(tetrahydrofuran) in cyclohexane (440 ml) under nitrogen atmosphere at −70° C. over 1 hour, then into the solution was bubbled sulfur dioxide for 1.5 hours at −70° C. After stirring for 1 hour at room temperature, the solvent was removed in vacuo and ether was added to the residue. The formed precipitate was separated by filtration to give a mixture of lithium 4,5-dichlorobenzo[b]furan-2-sulfinate and lithium 5,6-dichlorobenzo[b]furan-2sulfinate. To the suspension of the products in dichloromethane (1.8 l) was added N-chlorosuccinimide (92.1 g) at -50° C. and stirred for 1.5 hours. At room temperature, insoluble matters were filtered off and dichloromethane was removed in vacuo and the residue was purified by silica gel column chromatography to give 17.4 g of 4,5-dichlorobenzo[b]furan-2-ylsulfonyl chloride and 7.4 g of 5,6-dichlorobenzo[b]furan-2-ylsulfonyl chloride, respectively. 4,5-dichlorobenzo[b]furan-2-ylsulfonyl chloride Melting point: 114.6° C.
IR (KBr, cm$^{-1}$): 1529, 1444, 1401, 1191
NMR (DMSO-d$_6$, ppm): 6.87 (1H, d, J=1.0 Hz),
7.55 (1H, d, J=8.9 Hz),
7.69 (1H, dd, J=8.9, 1.0 Hz) 5,6-dichlorobenzo[b]furan-2-ylsulfonyl chloride
Melting point: 159.8° C.
IR (KBr, cm$^{-1}$): 1537, 1390, 1163, 1081
NMR (DMSO-d$_6$, ppm): 6.87 (1H, d, J=1.0 Hz),
7.92 (1H, s), Step 4

Preparation of N-(4,5-dichlorobenzo[b]furan-2-ylsulfonyl)glycine ethyl ester.

Starting from 4,5-dichlorobenzo[b]furan-2-ylsulfonyl chloride obtained in Step 3 (17 g), the objective compound (18.2 g) was obtained in a manner similar to Step 2 of Example 91.

Melting point: 155.2–155.5° C.
IR (KBr, cm$^{-1}$): 3199, 1737, 1225, 1160
NMR (CDCl$_3$, ppm): 1.05 (3H, t, J=7.1 Hz),
3.92 (2H, s), 3.95 (2H, q,
J=7.1 Hz), 7.56 (1H, s),
7.78 (2H, s), 9.09 (1H, bs)

Step 5

Preparation of N-(4,5-dichlorobenzo[b]furan-2-ylsulfonyl)glycine.

Starting from the product obtained in Step 4 (18 g), the objective compound (16.2 g) was obtained in a manner similar to Step 3 of Example 91.

Melting point: 189.8–194.7° C.
IR (KBr, cm$^{-1}$): 3320, 1719, 1366, 1256, 1162
NMR (DMSO-d$_6$, ppm): 3.83 (2H, d, J=6.3 Hz),
7.56 (1H, s),
7.76 (2H, s),
8.97 (1H, t, J=6.3 Hz)

Step 6

Preparation of 1-(4,5-dichlorobenzo[b]furan-2-ylsulfonyl)-2-thiohydantoin.

Starting from the product obtained in Step 5 (16 g), the objective compound (7.4 g) was obtained in a manner similar to Step 4 of Example 91.

Melting point: 214.6–217.5° C.
IR (KBr, cm$^{-1}$): 1793, 1762, 1445, 1167
NMR (DMSO-d$_6$, ppm): 4.77 (2H, s), 7.85 (2H, s),
8.11 (1H, s), 12.95 (1H, bs)

Step 7

Preparation of 1-(4,5-dichlorobenzo[b]furan-2-ylsulfonyl)hydantoin.

To a suspension of iodine monochloride (6.3 ml) in 1 M hydrochloric acid (150 ml) were added successively the product obtained in Step 6 (7.3 g) and dropwise dichloromethane (150 ml) over 10 minutes. The mixture was stirred for 2.5 hours at room temperature. Under ice-cooling, to the solution was added saturated aqueous sodium sulfite solution and stirred for a while. The formed precipitate was separated by filtration and washed with successive water, ethanol and ether to give 4.8 g of the objective compound.

Melting point: 290.7–292.0° C. (decomposition)
IR (KBr, cm$^{-1}$): 3256, 1742, 1391, 1356, 1168
NMR (DMSO-d$_6$, ppm): 4.47 (2H, s), 7.85 (2H, s),
7.98 (1H, s), 11.80 (1H, bs)

EXAMPLE 95

Preparation of 1-(5,6-dichlorobenzo[b]furan-2-ylsulfonyl)hydantoin (compound 45).

Step 1

Preparation of N-(5,6-dichlorobenzo[b]furan-2-ylsulfonyl)glycine ethyl ester.

To a solution of 5,6-dichlorobenzo[b]furan-2-ylsulfonyl chloride obtained in Step 3 of Example 64 (7.4 g) in dichloromethane (60 ml) was added glycine ethyl ester hydrochloride (7.95 g) and added slowly triethylamine (7.89 ml) under ice-cooling and nitrogen atmosphere. The resulting solution was poured into water (100 ml) and acidified with 1 M hydrochloric acid and extracted with ethyl acetate. The organic layer was washed with saturated aqueous NaCl solution and dried over anhydrous sodium sulfate. Ethyl acetate was removed in vacuo and the residue was washed with hexane to give 8.7 g of the objective compound.

Melting point: 132.7–133.5° C.
IR (KBr, cm$^{-1}$): 3227, 1735, 1360, 1225, 1158
NMR (DMSO-d$_6$, ppm): 1.06 (3H, t, J=6.9 Hz),
3.90 (2H, s), 3.95 (2H, q,
J=6.9 Hz), 7.52 (1H, s),
8.08 (1H, s), 8.20 (1H, s),
9.05 (1H, bs)

Step 2

Preparation of N-(5,6-dichlorobenzo[b]furan-2-ylsulfonyl)glycine.

Starting from the product obtained in Step 1 (8.6 g), the objective compound (7.8 g) was obtained in a manner similar to Step 3 of Example 91.

Melting point: 192.6–201.8° C.
IR (KBr, cm$^{-1}$): 3367, 1719, 1359, 1248, 1159
NMR (DMSO-d$_6$, ppm): 3.80 (2H, d, J=5.9 Hz),
7.51 (1H, d, J=1.0 Hz),
8.08 (1H, s),
8.19 (1H, d, J=1.0 Hz),
8.92 (1H, t, J=5.9 Hz)

Step 3

Preparation of 1-(5,6-dichlorobenzo[b]furan-2-ylsulfonyl)-2-thiohydantoin.

Starting from the product obtained in Step 2 (7.7 g), the objective compound (3.7 g) was obtained in a manner similar to Step 4 of Example 91.

Melting point: >246.0° C. (decomposition)
IR (KBr, cm$^{-1}$): 3100, 1743, 1449, 1246, 1166
NMR (DMSO-d$_6$, ppm): 4.73 (2H, s), 8.02 (1H, d, J=1.0 Hz), 8.20 (1H, s),
8.26 (1H, d, J=1.0 Hz),
12.82 (1H, bs)

Step 4

Preparation of 1-(5,6-dichlorobenzo[b]furan-2-ylsulfonyl)hydantoin.

Starting from the product obtained in Step 3 (3.7 g), the objective compound (2.7 g) was obtained in a manner similar to Step 5 of Example 91.

Melting point: >300° C. (decomposition)
IR (KBr, cm$^{-1}$): 1732, 1389, 1186, 1167
NMR (DMSO-d , ppm): 4.31 (2H, s), 7.82 (1H, d, J=0.7 Hz), 8.16 (1H, s),
8.27 (1H, d, J=0.7 Hz)

EXAMPLE 96

Preparation of 1-(3-bromo-7-fluorobenzo[b]furan-2-ylsulfonyl)hydantoin (compound 49).

Step 1

Preparation of 2,3-dibromo-2,3-dihydro-7-fluorobenzo[b]furan.

To a solution of 7-fluorobenzo[b]furan (16 g) in carbon tetrachloride (40 ml) was added dropwise a solution of bromine (22 g) in carbon disulfide (40 ml) at −30° C. and the solution was stirred for 1 hour. At room temperature, the formed precipitate was separated by filtration to give 34.4 g of the objective compound.

IR (KBr, cm$^{-1}$): 1634, 1601, 1489, 1459, 1279, 1179
NMR (CDCl$_3$, ppm): 5.74 (1H, d, J=1.3 Hz),
6.93 (1H, s),
7.11–7.35 (3H, m)

Step 2

Preparation of 3-bromo-7-fluorobenzo[b]furan.

To a solution of potassium hydroxide (12.7 g) in ethanol (180 ml) was slowly added the product obtained in Step 1 (34 g) and stirred for 3 hours. The resulting solution was neutralized by acetic acid, then extracted with ether. The organic layer was washed with successive water and saturated aqueous NaCl solution. After drying over anhydrous sodium sulfate, ether was removed in vacuo to give 24.1 g of the objective compound.

IR (neat, cm$^{-1}$): 3150, 1636, 1595, 1494, 1434, 1322
NMR (CDCl,, ppm): 6.98–7.36 (3H, m),
7.68 (1H, s)

Step 3

Preparation of 3-bromo-7-fluorobenzo[b]furan-2-ylsulfonyl chloride.

Starting from the product obtained in Step 2 (24.1 g), the objective compound (12.2 g) was obtained in a manner similar to Step 1 of Example 91.

IR (KBr, cm$^{-1}$): 1602, 1533, 1385, 1168
NMR (DMSO-d$_6$, ppm): 7.33–7.39 (3H, m)

Step 4

Preparation of N-(3-bromo-7-fluorobenzo[b]furan-2-ylsulfonyl)glycine ethyl ester.

Starting from the product obtained in Step 3 (12.2 g), the objective compound (10.2 g) was obtained in a manner similar to Step 2 of Example 91.

Melting point: 126.2–126 4° C.
IR (KBr, cm$^{-1}$): 3200, 1731, 1366, 1237, 1142
NMR (DMSO-d$_6$, ppm): 1.01 (3H, t, J=7.1 Hz),
3.89 (2H, q, J=7.1 Hz),
3.96 (2H, d, J=5.6 Hz),
7.47–7.66 (3H, m),
9.32 (1H, t, J=5.6 Hz)

Preparation of N-(3-bromo-7-fluorobenzo[b]furan-2-ylsulfonyl)glycine.

Starting from the product obtained in Step 4 (10.2 g), the objective compound (7.25 g) was obtained in a manner similar to Step 3 of Example 91.

IR (KBr, cm$^{-1}$): 3223, 1716, 1373, 1246, 1163
NMR (DMSO-d$_6$, ppm): 3.86 (2H, s),
7.46–7.58 (3H, m),
9 18 (1H, bs)

Preparation of 1-(3-bromo-7-fluorobenzo[b]furan-2-ylsulfonyl)-2-thiohydantoin.

Starting from the product obtained in Step 5 (7.2 the objective compound (5.07 g) was obtained in a manner similar to Step 4 of Example 91.

Melting point: 224.3–224.7° C. (decomposition)
IR (KBr, cm$^{-1}$): 3290, 1793, 1765, 1235, 1141
NMR (DMSO-d$_6$, ppm): 4.83 (2H, s),
7.57–7.72 (3H, m),
12.93 (1H, bs)

Step 7

Preparation of 1-(3-bromo-7-fluorobenzo[b]furan-2-ylsulfonyl)hydantoin.

To a suspension of iodine monochloride (3.3 ml) in 1 M hydrochloric acid (110 ml) was added the product obtained in Step 6 (5 g) and dropwise dichloromethane (140 ml). The mixture was stirred for 6 hours at room temperature and then additive iodine monochloride (1.7 ml) was added to the mixture and the resulting mixture was stirred for 1 hour. To the resulting solution was added saturated aqueous sodium sulfite solution and formed precipitate was separated by filtration. The organic layer was washed with saturated aqueous NaCl solution and dried over anhydrous magnesium sulfate. Formed precipitate was suspended in 1 M hydrochloric acid (100 ml) and the suspension was extracted with ethyl acetate. The organic layer was washed with saturated aqueous NaCl solution and dried over anhydrous magnesium sulfate. Both extracts were combined and the solvent was removed in vacuo. The resulting residue was washed with successive ethanol and ether to give 1.66 g of the objective compound.

Melting point: 266.6–270.6° C.
IR (KBr, cm$^{-1}$): 3160, 1725, 1393, 1184, 1149
NMR (DMSO-d$_6$, ppm): 4.50 (2H, s), 7.53–7.77 (3H, m), 11.85 (1H, bs)

Compounds of Example 97 to 102 prepared in a manner similar to Example 91 are summarized in the following table 11 together with corresponding IR and NMR data and melting points.

TABLE 11

Q—SO₂—N(CH₂C(=O))(C(=O)NH) (cyclic imide)

| Ex. No. | Q | IR(KBr, cm⁻¹) | NMR(DMSO-d₆, ppm) | M.P. (°C.) |
|---|---|---|---|---|
| 97 | 6-Br-benzofuran-2-yl | 1732, 1389, 1181, 1166 | 4.32(2H, s), 7.59(1H, dd, J=8.6, 1.7Hz), 7.82(1H, d, J=8.6Hz), 7.87(1H, d, J=1.7Hz), 8.12(1H, s) | >297 (dec.) |
| 98 | 3-I-benzofuran-2-yl | 3216, 1734, 1397, 1363, 1175, 1151 | 4.54(2H, s), 7.51~7.75(4H, m), 11.82(1H, bs) | 292 (dec.) |
| 99 | 3,4-diBr-benzofuran-2-yl | 1742, 1394, 1183, 1174, 1153 | 4.55(2H, s), 7.55(1H, t, J=7.9Hz), 7.74(1H, dd, J=7.9, 1.3Hz), 7.91(1H, dd, J=7.9, 1.3Hz), 11.87(1H, bs) | 256.3~258.6 (dec.) |
| 100 | 3,6-diBr-benzofuran-2-yl | 3262, 1734, 1397, 1352, 1178, 1170 | 4.44(2H, s), 7.70(1H, d, J=1.0Hz), 7.71(1H, s), 8.22(1H, d, J=1.0Hz) | >249.2 (dec.) |
| 101 | 3-Br-4,6-diCl-benzofuran-2-yl | 3279, 1744, 1404, 1176, 1148 | 4.51(2H, s), 7.74(1H, d, J=1.7Hz), 8.16(1H, d, J=1.7Hz), 11.82(1H, bs) | 249.5~251.7 |
| 102 | 3-CF₃-benzofuran-2-yl | 3220, 1745, 1407, 1357, 1181, 1152 | 4.48(2H, s), 7.58~7.97(4H, m) | 238.8~240.8 |

Another intermediate compounds of Example 29 to 39, 41 to 48, 50, 52, 54, 63 to 83, 97 to 102 are summarized in the following table 12 to 16 together with corresponding IR and NMR data and melting points.

TABLE 12

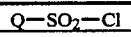

| Ex. No. | Q | IR(KBr,cm⁻¹) | NMR(DMSO-d₆,ppm) | M.P. (°C.) |
|---|---|---|---|---|
| 29 | 5-F-benzothiophen-2-yl | 1500,1392, 1216,1174, 1001 | 7.12~8.00(3H,m), 7.43(1H,s) | |
| 30 | 5-Cl-benzothiophen-2-yl | 1588,1493, 1169,1078 | 7.55(1H,dd, J=8.9,1.3Hz), 7.85(1H,d,J=8.9Hz), 7.95(1H,d,J=1.3Hz), 8.07(1H,s)* | |
| 31 | 3-Cl-benzothiophen-2-yl | 1592,1480, 1391,1248, 1180 | 7.37~8.01(4H,m) | |

TABLE 12-continued
Q—SO$_2$—Cl
| Ex. No. | Q | IR(KBr,cm$^{-1}$) | NMR(DMSO-d$_6$,ppm) | M.P. (°C.) |
|---|---|---|---|---|
| 32 | 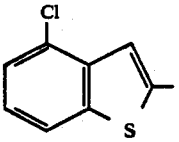 | 1584,1544, 1493,1388, 1170,1007 | 7.35~7.95(3H,m), 7.42(1H,s) | |
| 33 | 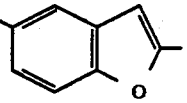 | 1530,1372, 1275,1240, 1160 | 7.46~7.92(3H,m), 7.58(1H,s)* | |
| 34 | 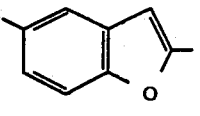 | 1531,1394, 1164,1080, 809 | 7.50~7.76(3H,m), 7.59(1H,s)* | |
| 35 | 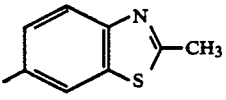 | 1508,1406, 1375,1320, 1180 | 2.81(3H,s), 7.74~8.24(3H,m) | |
| 37 | 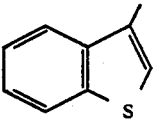 | 1423,1375, 1172 | 7.38~7.72(2H,m), 7.84~8.01(1H,m), 8.26~8.46(1H,m), 8.51(1H,s)* | |
| 38 | 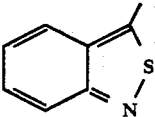 | 1383,1170, 750,590 | 7.53~7.72(2H,m), 7.87~8.03(1H,m), 8.07~8.23(1H,m)* | |
| 39 | 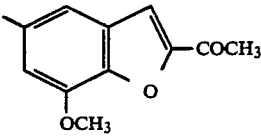 | | 2.67(3H,s), 4.13(3H,s), 7.51~8.08(3H,m)* | |
| 41 | 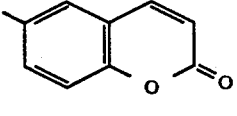 | 1734,1375, 1169,1102 | 6.51(1H,d,J=9.6Hz), 7.36(1H,d,J=8.6Hz), 7.85(1H,dd, J=8.6,2.0Hz), 8.02(1H,d,J=2.0Hz), 8.16(1H,d,J=9.6Hz) | |
| 42 | 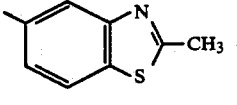 | 1415,1381, 1371,1237, 1172,1151 | 2.81(3H,s), 7.60~8.06(3H,m), | |
| 43 | 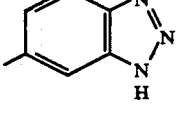 | 1617,1383, 1371,1216, 1173 | 7.70(1H,dd, J=8.6,1.0Hz), 7.87(1H,d,J=8.6Hz), 8.08(1H,d,J=1.0Hz) | |
| 44 | 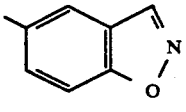 | 1604,1380, 1192,1161, 534 | 7.86(1H,d,J=8.9Hz), 8.27(1H,dd, J=8.9,2.0Hz), 8.55(1H,d,J=2.0Hz), 3.93(1H,s)* | |

TABLE 12-continued
| Ex. No. | Q | IR(KBr,cm$^{-1}$) | NMR(DMSO-d$_6$,ppm) | M.P. (°C.) |
|---|---|---|---|---|
| 45 | 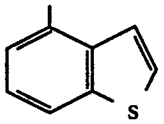 | 1379,1368, 1314,1171, 1158 | 7.50(1H,t,J=7.9Hz), 7.82(1H,d,J=5.6Hz), 8.00~8.28(3H,m)* | |
| 46 | 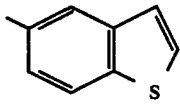 | 1375,1311, 1202,1169, 1043 | 7.47~8.15(5H,m) | |
| 47 | 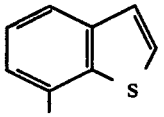 | | 7.35~7.90(5H,m) | |
| 48 | 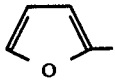 | 1457,1395, 1214,1166 | 7.05~7.14(2H,m), 8.21~8.24(1H,m) | |
| 50 | 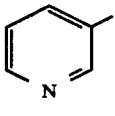 | 1625,1590, 1522,1377, 1175 | 8.00~8.98(4H,m) | |
| 52 | 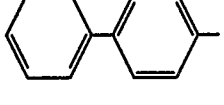 | 1590,1374, 1178, 765 | 7.36~7.78(9H,m) | |
| 54 | 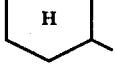 | 2945,2941, 1453,1373, 1161 | 1.23~2.50(10H,m), 3.39~3.65(1H,m)* | |
| 63 | 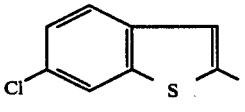 | 1479,1380, 1166,1000, 548 | 7.37(1H,dd, J=8.6,1.3Hz), 7.44(1H,s), 7.84(1H,d,J=8.6Hz), 8.04(1H,d,J=1.3Hz) | |
| 64 | 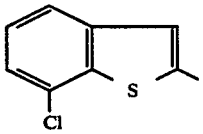 | 1493,1454, 1390,1167 | 7.32~7.53(2H,m), 7.62(1H,s), 7.82~7.97(1H,m) | |
| 65 |  | 2968,2935, 1503,1465, 1375,1167 | 1.59(3H,d,J=7.3Hz), 4.11~4.44(1H,m), 7.44~7.64(2H,m), 7.83~7.94(1H,m), 8.15~8.26(1H,m)* | |
| 66 | 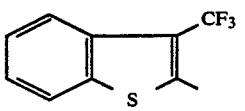 | | 7.42~8.06(4H,m) | |
| 67 | 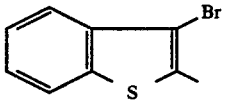 | 1473,1389, 1177, 533 | 7.51~8.11(4H,m)* | |

TABLE 12-continued

Q—SO$_2$—Cl

| Ex. No. | Q | IR(KBr, cm$^{-1}$) | NMR(DMSO-d$_6$, ppm) | M.P. (°C.) |
|---|---|---|---|---|
| 68 | 2-methyl-3-(ethoxycarbonylmethyl)benzo[b]thiophene | 1737, 1371, 1329, 1201, 1174 | 1.17(3H,t,J=7.3Hz), 4.05(2H,q,J=7.3Hz), 4.20(2H,s), 7.29~7.39(2H,m), 7.58~7.64(1H,m), 7.82~7.88(1H,m) | 90.4~ 93.2 (dec.) |
| 70 | 4,6-dichloro-2-methylbenzofuran | 1575, 1530, 1394, 1384, 1174 | 7.47~7.69(3H,m)* | 116.0~ 116.9 |
| 71 | 3-bromo-2-methylbenzofuran | 1520, 1395, 1231, 1148 | 7.31~7.67(4H,m) | |
| 72 | 3,4-dibromo-2-methylthiophene | 1396, 1178, 1049 | 7.73(1H,s) | 101.3~ 103.0 |
| 73 | 3-bromo-7-fluoro-2-methylbenzo[b]thiophene | 1488, 1384, 1174, 570 | 7.26~7.92(3H,m)* | 90.0~ 92.0 |
| 74 | 2-methyl-4,5,6,7-tetrahydrobenzo[b]thiophene | 2948, 1436, 1417, 1166 | 1.79~1.94(4H,m), 2.62~2.85(4H,m), 7.55(1H,s)* | |
| 75 | 2-methyl-3-phenylbenzofuran | 1398, 1242, 1182, 1147, 534 | 7.31~7.70(9H,m)* | 76.2~ 77.4 |
| 76 | 3-fluoro-2-methylbenzo[b]thiophene | 1526, 1389, 1370, 1179, 570, 538 | 7.42~8.27(4H,m)* | |
| 77 | 3-fluoro-2-methylthiophene | | 6.96(1H,d,J=5.6Hz), 7.66~7.77(1H,m)* | |
| 78 | 2-chloro-3-methylbenzo[b]thiophene | 1478, 1419, 1383, 1178 | 7.42~8.41(4H,m)* | |
| 79 | 2-methyl-3-nitrobenzo[b]thiophene | | 7.45~7.85(3H,m), 8.40~8.50(1H,m)* | |

TABLE 12-continued

Q—SO₂—Cl

| Ex. No. | Q | IR(KBr,cm⁻¹) | NMR(DMSO-d₆,ppm) | M.P. (°C.) |
|---|---|---|---|---|
| 80 | 4-iodo-2-methylbenzofuran | 1381, 1161, 1086, 775 | 7.24~7.85(4H,m)* | |
| 82 | 3-(SCH₃)-2-methylbenzothiophene | 1377, 1172, 1164, 762, 567 | 2.58(3H,s), 7.46~8.25(4H,m)* | |
| 83 | 3-(OCH₃)-2-methylbenzothiophene | 1510, 1377, 1348, 1175, 578 | 4.09(3H,s), 7.36~7.74(4H,m) | |
| 97 | 6-bromo-2-methylbenzofuran | 1533, 1385, 1168, 1077 | 7.49~7.71(3H,m), 7.86(1H,s)* | 82.1~82.9 |
| 98 | 3-iodo-2-methylbenzofuran | 1507, 1501, 1391, 1225, 1139 | 7.38~7.88(4H,m)* | 88.3~91.6 |
| 101 | 4,6-dichloro-3-bromo-2-methylbenzofuran | | 7.46(1H,d,J=1.7Hz), 7.61(1H,d,J=1.7Hz)* | |
| 102 | 3-CF₃-2-methylbenzofuran | | 7.46~7.99(4H,m)* | |

NMR data marked with asterisks (*) were measured in CDCl₃.

TABLE 13

Q—SO₂NHCH₂COOEt

| Ex. No. | Q | IR(KBr, cm⁻¹) | NMR(DMSO-d₆, ppm) | M.P. (C.) |
|---|---|---|---|---|
| 97 | 6-bromo-2-methylbenzofuran | 3340, 1742, 1357, 1204, 1161 | 1.18(3H, t, J=7.3Hz), 3.96(2H, d, J=5.6Hz), 4.10(2H, q, J=7.3Hz), 5.51(1H, t, J=5.6Hz), 7.35~7.73(4H, m) | 81.2~81.5 |
| 98 | 3-iodo-2-methylbenzofuran | 3184, 1738, 1364, 1225 | 1.00(3H, t, J=7.1Hz), 3.87(2H, q, J=7.1Hz), 3.92(2H, d, J=5.9Hz), 7.45~7.90(4H, m), 9.03(1H, t, J=5.9Hz) | 130.4~134.1 |
| 99 | 4-bromo-3-bromo-2-methylbenzofuran | 3197, 1737, 1366, 1229, 1162 | 1.19(3H, t, J=7.1Hz), 4.02(2H, d, J=6.6Hz), 4.10(2H, d, J=7.1Hz), 5.64(1H, t, J=6.6Hz), 7.24~7.63(3H, m) | 129.4~130.6 |
| 100 | 6-bromo-3-bromo-2-methylbenzofuran | 3295, 1732, 1366, 1232, 1147 | 1.18(3H, t, J=7.1Hz), 4.01(2H, d, J=6.6Hz), 4.08(2H, q, J=7.1Hz), 5.62(1H, t, J=6.6Hz), 7.52(2H, s), 7.74(1H, s) | 132.9~133.4 |

TABLE 13-continued

Q—SO₂NHCH₂COOEt

| Ex. No. | Q | IR(KBr, cm⁻¹) | NMR(DMSO-d₆, ppm) | M.P. (°C.) |
|---|---|---|---|---|
| 101 | 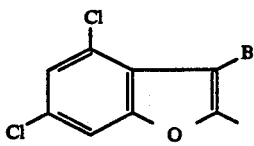 | 3236, 1731, 1365, 1233, 1148 | 1.20(3H, t, J=7.1Hz), 4.02(2H, d, J=4.9Hz), 4.11(2H, q, J=7.1Hz), 5.62(1H, t, J=4.9Hz), 7.38(1H, d, J=1.7Hz), 7.51(1H, d, J=1.7Hz) | 167.3~169.2 |
| 102 | 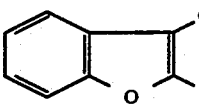 | 3203, 1739, 1371, 1228, 1171 | 1.00(3H, t, J=6.9Hz), 3.90(2H, q, J=6.9Hz), 3.99(2H, d, J=6.6Hz), 7.44~7.89(4H, m), 9.39(1H, t, J=6.6Hz) | 135.6~147.8 |

TABLE 14

Q—SO₂NHCH₂CO₂H

| Ex. No. | Q | IR(KBr, cm⁻¹) | NMR(DMSO-d₆, ppm) | M.P. (°C.) |
|---|---|---|---|---|
| 63 | 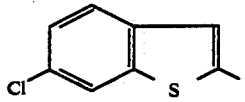 |  | 3.74(2H, s), 7.48~8.27(4H, m), 8.55(1H, bs) | 210.1~213.3 |
| 64 | 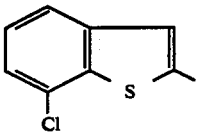 | 3270, 1732, 1394, 1354, 1260, 1160 | 3.76(2H, d, J=5.9Hz), 7.38~8.09(4H, m), 8.65(1H, t, J=5.9Hz), 12.74(1H, bs) | 193.0~205.0 |
| 65 | 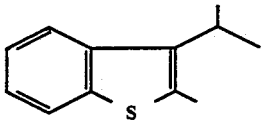 | 3312, 2980, 2968, 1726, 1321, 1143 | 1.45(6H, d, J=7.3Hz), 3.72(2H, d, J=4.3Hz), 3.84~4.17(1H, m), 7.42~8.30(4H, m), 8.61(1H, t, J=4.3Hz) | 110.0~115.5 |
| 66 | 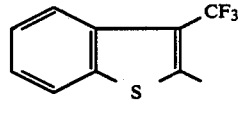 | 3354, 1730, 1421, 1361, 1214, 1164, 1122 | 3.73(2H, s), 7.57~8.25(4H, m) | 141.3~144.5 |
| 67 | 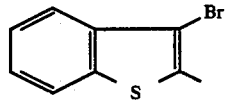 | 3304, 1725, 1709, 1487, 1353, 1249, 1160 | 3.86(2H, d, J=5.9Hz), 7.57~8.19(4H, m), 8.81(1H, t, J=5.9Hz) | 149.1~153.3 |
| 68 | 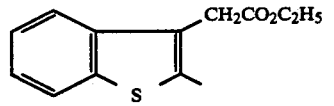 | 3294, 1735, 1158 | 1.17(3H, t, J=7.1Hz), 3.67(2H, d, J=6.3Hz), 4.08(2H, q, J=7.1Hz), 4.28(2H, s), 7.46~8.11(4H, m), 8.64(1H, t, J=6.3Hz) | 125.0~126.9 |
| 69 | 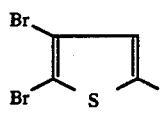 | 3280, 1734, 1372, 1347, 1312, 1255, 1167 | 3.72(2H, d, J=5.3Hz), 7.61(1H, s), 8.55(1H, t, J=5.3Hz), 12.85(1H, bs) | 200.5~202.0 |
| 70 | 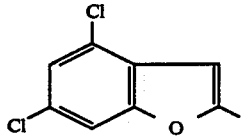 | 3275, 1718, 1364, 1161 | 3.82(2H, d, J=5.9Hz), 7.53(1H, s), 7.63(1H, d, J=1.6Hz), 7.99(1H, bs), 8.95(1H, t, J=5.9Hz) | 194.2~196.4 |
| 71 | 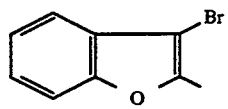 | 1717, 1709, 1437, 1369, 1150 | 3.82(2H, d, J=5.9Hz), 7.36~7.80(4H, m), 8.95(1H, t, J=5.9Hz) | 153.4~156.1 |

TABLE 14-continued
Q—SO₂NHCH₂CO₂H
| Ex. No. | Q | IR(KBr, cm⁻¹) | NMR(DMSO-d₆, ppm) | M.P. (°C.) |
|---|---|---|---|---|
| 72 | 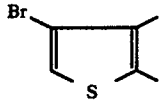 | 3340, 1718, 1321, 1252, 1153, 1141, 1130 | 3.79(2H, d, J=5.9Hz), 8.17(1H, s), 8.72(1H, t, J=5.9Hz), 12.82(1H, bs) | 203.5~205.2 |
| 73 | 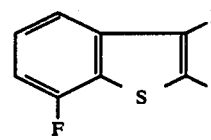 | 3344, 1713, 1498, 1341, 1247, 1163 | 3.88(2H, d, J=6.3Hz), 7.43~7.82(3H, m), 8.98(1H, t, J=6.3Hz) | 194.0~201.0 |
| 74 | 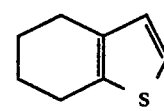 | 3315, 3201, 2433, 1752, 1443, 1326, 1187, 1158 | 1.50~1.98(4H, m), 2.40~2.88(4H, m), 3.59(2H, d, J=4.9Hz), 7.26(1H, s), 8.08(1H, t, J=4.9Hz) | 141.2~143.2 |
| 75 | 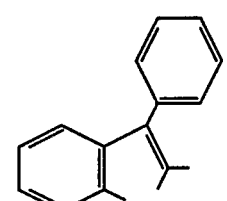 | 3265, 1716, 1352, 1236, 1169, 1139 | 3.74(2H, s), 7.08~7.81(9H, m), 8.72(1H, bs) | 151.4~153.7 |
| 76 | 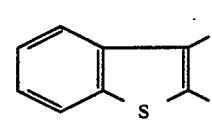 | 3290, 1742, 1375, 1255, 1173, 1118 | 3.82(2H, d, J=5.9Hz), 7.45~8.16(4H, m), 8.84(1H, t, J=5.9Hz), 12.72(1H, bs) | 129.7~134.2 |
| 77 | 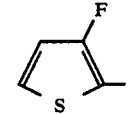 | 3306, 3117, 1732, 1546, 1424, 1412, 1336, 1160 | 3.73(2H, d, J=5.9Hz), 7.11(1H, d, J=5.6Hz), 7.86(1H, dd, J=5.6, 4.3Hz), 8.54(1H, t, J=5.9Hz), 12.72(1H, bs) | 167.4~169.4 |
| 78 | 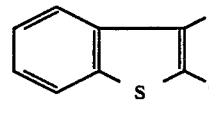 | 3264, 1725, 1420, 1350, 1249, 1160 | 3.74(2H, d, J=5.6Hz), 7.45~8.31(4H, m), 8.60(1H, t, J=5.6Hz), 12.51(1H, bs) | 126.0~129.5 |
| 79 | 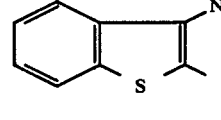 | 1747, 1589, 1367, 1198 | 4.30(2H, d, J=5.9Hz), 7.21~8.34(4H, m), 9.94(1H, t, J=5.9Hz) | 212.4 (dec.) |
| 80 | 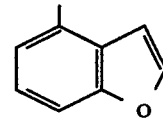 | 3265, 1717, 1362, 1248, 1159 | 3.83(2H, d, J=5.9Hz), 7.22~7.84(4H, m), 8.85(1H, t, J=5.9Hz), 12.66(1H, bs) | 222.9~227.1 |
| 81 | 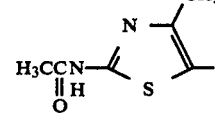 | 3290, 1707, 1560, 1338, 1167 | 2.16(3H, s), 2.43(3H, s), 3.65(2H, d, J=6.3Hz), 8.27(1H, t, J=6.3Hz), 12.45(1H, bs) | 247.0 (dec.) |
| 97 | 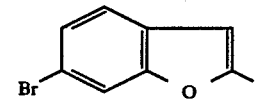 | 3312, 1719, 1353, 1249, 1165 | 3.77(2H, s), 7.49~7.79(3H, m), 8.04(1H, s), 8.79(1H, bs) | 186.5 |

TABLE 14-continued

Q—SO$_2$NHCH$_2$CO$_2$H

| Ex. No. | Q | IR(KBr, cm$^{-1}$) | NMR(DMSO-d$_6$, ppm) | M.P. (°C.) |
|---|---|---|---|---|
| 98 | benzofuran with I at 3-position | 3230, 1709, 1368, 1238, 1173 | 3.82(2H, d, J=5.9Hz), 7.44~7.73(4H, m), 8.88(1H, t, J=5.9Hz) | 179.4~183.0 |
| 99 | benzofuran with Br at 4-position and Br at 3-position | 3280, 1716, 1369, 1238, 1168 | 3.85(2H, bs), 7.47(1H, dd, J=7.9, 7.6Hz), 7.68(1H, dd, J=7.6, 1.3Hz), 7.83(1H, dd, J=7.9, 1.3Hz), 9.00(1H, bs) | 222.9~227.1 |
| 100 | benzofuran with Br at 3-position and Br at 6-position | 3338, 1731, 1365, 1234, 1166 | 3.83(2H, bs), 7.63(2H, s), 8.14(1H, s), 9.00(1H, bs) | 210.4~212.0 |
| 101 | benzofuran with Cl at 4-position, Cl at 6-position and Br at 3-position | 3238, 1717, 1369, 1171, 1151 | 3.86(2H, d, J=6.3Hz), 7.66(1H, d, J=1.7Hz), 8.07(1H, d, J=1.7Hz), 9.15(1H, t, J=6.3Hz) | 239.1~241.3 |
| 102 | benzofuran with CF$_3$ at 3-position | 3247, 1716, 1373, 1239, 1173 | 3.89(2H, d, J=6.3Hz), 7.50~7.91(4H, m), 9.30(1H, t, J=6.3Hz) | 162.0~178.1 |

TABLE 15

Q—SO$_2$NHCH$_2$CONH$_2$

| Ex. No. | Q | IR(KBr,cm$^{-1}$) | NMR(DMSO-d$_6$,ppm) | M.P. (°C.) |
|---|---|---|---|---|
| 82 | benzothiophene with SCH$_3$ | 3434,3308, 3188,1703, 1366,1155 | 2.46(3H,s), 3.67(2H,d,J=4.6Hz), 7.10(1H,bs), 7.30(1H,bs), 7.53~8.16(5H,m) | 180.4~181.1 |
| 83 | benzothiophene with OCH$_3$ | 3392,1672, 1522,1354, 1333,1153, 1139 | 3.60(2H,s), 4.10(3H,s), 7.05(1H,bs), 7.20(1H,bs), 7.53~8.16(5H,m) | 162.0~163.1 |

TABLE 16

$$Q-SO_2-N\underset{S}{\overset{}{\underset{\|}{C}}}\hspace{-2pt}\diagdown NH \text{ (thiazolidine-2-thione-dione ring)}$$

| Ex. No. | Q | IR(KBr,cm$^{-1}$) | NMR(DMSO-d$_6$,ppm) | M.P. (°C.) |
|---|---|---|---|---|
| 63 | benzothiophene with Cl | 3320,1800, 1769,1458, 1370,1230 | 4.74(2H,s), 7.58(1H,dd, J=8.6,1.7Hz), 8.11(1H,d,J=8.6Hz), 8.36(1H,d,J=1.7Hz), 8.47(1H,s), 12.75(1H,bs) | 249.6 (dec.) |

TABLE 16-continued

Q—SO$_2$—N(CH$_2$C(=O))—C(=S)—NH (thiazolidine-dione-like structure)

| Ex. No. | Q | IR(KBr,cm$^{-1}$) | NMR(DMSO-d$_6$,ppm) | M.P. (°C.) |
|---|---|---|---|---|
| 64 | 7-chlorobenzothiophen-2-yl | 3110,1791, 1751,1745, 1381,1180 | 4.76(2H,s), 7.50~7.82(1H,m), 8.11(1H,dd, J=7.6,1.3Hz), 8.57(1H,s), 12.79(1H,bs) | 221.0 (dec.) |
| 65 | 3-isopropylbenzothiophen-2-yl | 3140,1791, 1757,1459, 1346,1177 | 1.43(6H,d,J=6.9Hz), 3.63~3.96(1H,m), 7.47~7.61(1H,m), 8.07~8.31(1H,m), 12.84(1H,bs) | 191.3~ 195.7 |
| 66 | 3-(trifluoromethyl)benzothiophen-2-yl | 3120,1756, 1465,1366, 1175,1164 | 4.76(2H,s), 7.60~8.38(4H,m), 13.01(1H,bs) | 232.1~ 233.5 |
| 67 | 3-bromobenzothiophen-2-yl | 3180,1782, 1755,1455, 1372,1170 | 4.95(2H,s), 7.56~8.32(4H,m), 12.92(1H,bs) | 222.8 (dec.) |
| 68 | 3-(ethoxycarbonylmethyl)benzothiophen-2-yl | 3220,1756, 1726,1376, 1173 | 1.14(3H,t,J=7.1Hz), 4.05(2H,q,J=7.1Hz), 4.41(2H,s), 4.77(2H,s), 7.55~7.72(2H,m), 8.02~8.20(2H,m), 12.81(1H,bs) | 204.7 (dec.) |
| 69 | 4,5-dibromothiophen-2-yl | 1793,1473, 1392,1191, 1174 | 4.69(2H,s), 8.07(1H,s), 12.78(1H,bs) | 203.0 (dec.) |
| 70 | 4,6-dichlorobenzofuran-2-yl | 3292,1795, 1765,1464, 1381,1185, 1176 | 4.74(2H,s), 7.73(1H,d,J=1.7Hz), 8.06~8.09(2H,m), 12.87(1H,bs) | 211.6 (dec.) |
| 71 | 3-bromobenzofuran-2-yl | 1795,1759, 1460,1384, 1149 | 4.83(2H,s), 7.43~7.89(4H,m), 12.96(1H,bs) | 212.8~ 219.9 (dec.) |
| 72 | 3,5-dibromothiophen-2-yl | 3350,1793, 1764,1458, 1362,1174 | 4.87(2H,s), 8.44(1H,s), 12.88(1H,bs) | 242.0 (dec.) |
| 73 | 3-bromo-7-fluorobenzothiophen-2-yl | 3289,1795, 1770,1492, 1458,1359, 1180,1156, 1085 | 4.97(2H,s), 7.55~7.88(3H,m), 13.01(1H,bs) | 254.0 (dec.) |

TABLE 16-continued

Q—SO$_2$—N(C=S)(NH)—CH$_2$—C(=O)

| Ex. No. | Q | IR(KBr,cm$^{-1}$) | NMR(DMSO-d$_6$,ppm) | M.P. (°C.) |
|---|---|---|---|---|
| 74 | 4,5,6,7-tetrahydrobenzo[b]thiophen-2-yl | 3157,1794, 1765,1376, 1352,1161 | 1.50~1.92(4H,m), 2.46~2.94(4H,m), 4.65(2H,s), 7.72(1H,s), 12.61(1H,bs) | 245.0~ 246.8 |
| 75 | 3-phenylbenzofuran-2-yl | 1786,1750, 1446,1370, 1348,1178 | 4.37(2H,s), 7.13~7.90(9H,m), 12.82(1H,bs) | 183.8 (dec.) |
| 76 | 3-fluorobenzo[b]thiophen-2-yl | 3130,1790, 1759,1383, 1182 | 4.73(2H,s), 7.57~8.15(4H,m), 12.81(1H,bs) | 230.5~ 223.8 |
| 77 | 3-fluorothiophen-2-yl | 3107,1755, 1537,1469, 1423,1376, 1248,1173 | 4.66(2H,s), 7.21(1H,d,J=5.6Hz), 8.16(1H,dd, J=5.6,4.3Hz), | 194.4 (dec.) |
| 78 | 2-chloro-3-methylbenzo[b]thiophen-? | 3268,1790, 1765,1459, 1348,1178, 1160 | 4.93(2H,s), 7.50~7.73(2H,m), 8.04~8.29(2H,m), 12.82(1H,bs) | 244.0~ 246.0 |
| 79 | 3-nitrobenzo[b]thiophen-2-yl | 1790,1763, 1460,1348, 1182 | 4.68(2H,s), 7.59~7.70(2H,m), 8.14~8.40(2H,m), 12.68(1H,bs) | 170.0 (dec.) |
| 80 | 4-iodobenzofuran-2-yl | 3125,1744, 1456,1332, 1162 | 4.77(2H,s), 7.30~7.91(4H,m), 12.85(1H,bs) | 210.9 (dec.) |
| 81 | 2-acetamido-4-methylthiazol-5-yl | 3180,1761, 1535,1371, 1170 | 2.19(3H,s), 2.54(3H,s), 4.68(2H,s), 12.64(1H,bs), 12.75(1H,bs) | 250.0 (dec.) |
| 97 | 6-bromobenzofuran-2-yl | 3319,1794, 1766,1461, 1163 | 4.73(2H,s), 7.63(1H,d,J=8.6Hz), 7.85(1H,d,J=8.6Hz), 8.05(1H,s), 8.12(1H,s) | 246.8~ 247.7 |
| 98 | 3-iodobenzofuran-2-yl | 1735,1397, 1228,1173 | 4.88(2H,s), 7.56~7.90(4H,m), 13.04(1H,bs) | 195~ 198 |

TABLE 16-continued $$Q-SO_2-N\underset{S}{\overset{}{\bigvee}}\underset{NH}{\overset{O}{=}}$$

| Ex. No. | Q | IR(KBr,cm$^{-1}$) | NMR(DMSO-d$_6$,ppm) | M.P. (°C.) |
|---|---|---|---|---|
| 99 | benzofuran with Br at 4 and 3 positions, methyl | 3330,1792, 1764,1456, 1174 | 4.86(2H,s), 7.57(1H,t,J=7.9Hz), 7.75(1H,dd, J=7.9,1.3Hz), 7.93(1H,dd, J=7.9,1.3Hz), 13.08(1H,bs) | 219.5~ 222.3 |
| 100 | benzofuran with Br at 5 and 3 positions, methyl | 3084,1749, 1388,1266, 1182 | 4.81(2H,s), 7.70(1H,s), 7.72(1H,s), 8.22(1H,s) | >240 (dec.) |
| 101 | benzofuran with Cl at 4,6 and Br at 3, methyl | 3568,1752, 1382,1244, 1177 | 4.84(2H,s), 7.76(1H,d,J=1.6Hz), 8.17(1H,d,J=1.6Hz), 13.15(1H,bs) | 220 (dec.) |
| 102 | benzofuran with CF$_3$ at 3, methyl | 3110,1752, 1239,1178, 1174 | 4.83(2H,s), 7.60~7.99(4H,m) | 161.6~ 179.3 |

Formulation F (Capsules)

Compound 38, 250 g of weight, 730 g of lactose and 20 g of magnesium stearate were weighed and mixed until the mixture became homogeneous. The mixture was then filled in No. 1 hard gelatin capsule at 200 mg each to obtain capsule preparation.

Formulation G (Tablets)

Compound 34, 300 g of weight, 550 g of lactose, 120 g of potato starch, 15 g of polyvinyl alcohol and 15 g of magnesium stearate were weighed. The weighed amount of compound 34, lactose and potato starch were mixed until accomplishing homogeneity. Then aqueous solution of polyvinylalcohol was added to the mixture and granulated by wet process. The granules were then dried, mixed with magnesium stearate and pressed into tablets, each weighing 200 mg.

Formulation H (Powder)

Compound 46, 200 g of weight, 790 g of lactose and 10 g of magnesium stearate were weighed and mixed until the mixture became homogeneous to obtain 20% powder preparation.

Formulation I (Suppositories)

Compound 44, 100 g of weight were weighed and ground by a mortar until the compound became fine powder. Then 180 g of polyethylene glycol 1500 and 720 g of polyethylene glycol 4000 were added to the compound and melted. The mixture was then pressed at 1 g each to obtain suppository preparation.

What is claimed is:

1. A hydantoin derivative represented by the formula (I):

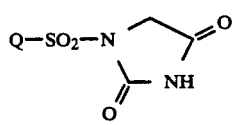

(I)

or a non-toxic salt, solvate or solvate of a non-toxic salt thereof; wherein Q represents a furyl group, a thienyl group, a benzofuryl group or a benzothienyl group, optionally substituted by one or more substituents which are the same or different and selected from a group consisting of a halogen atom, a lower alkyl group, a nitro group, a cyano group, an optionally protected carboxy group, an optionally protected carboxymethyl group, a halogenated lower alkyl group, a lower alkylthio group, a lower alkylcarbonyl group, a lower alkoxy group, a lower alkylsulfinyl group, a lower alkylsulfonyl group, an optionally protected hydroxy group, an optionally protected amino group, a carbamoyl group and a phenyl group.

2. A hydantoin derivative as claimed in claim 1 wherein Q represents an optionally substituted benzothien-2-yl group, or a toxic salt, solvate or solvate of a non-toxic salt thereof.

3. A hydantoin derivative as claimed in claim 1 wherein Q represents an optionally substituted benzofuran-2-yl group, or a non-toxic salt, solvate or solvate of a non-toxic salt thereof.

4. A hydantoin derivative as claimed in claim 3 wherein the said substituents are 1 to 3 halogen atoms.

5. A pharmaceutical composition for preventing or relieving diabetic complication which comprises a pharmaceutically acceptable carrier and an effective amount of at least one hydantoin derivative represented by the formula (I):

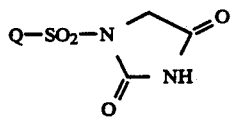

or a non-toxic salt, solvate or solvate of a non-toxic salt thereof; wherein Q represents a furyl group, a thienyl group, a benzofuryl group or a benzothienyl group, optionally substituted by one or more substituents which are same or different and selected from a group consisting of a halogen atom, a lower alkyl group, a nitro group, a cyano group, an optionally protected carboxy group, an optionally protected carboxymethyl group, a halogenated lower alkyl group, a lower alkylthio group, a lower alkylcarbonyl group, a lower alkoxy group, a lower alkylsulfinyl group, a lower alkylsulfonyl group, an optionally protected hydroxy group, an optionally protected amino group, a carbamoyl group and a phenyl group.

6. A pharmaceutical composition as claimed in claim 5 wherein Q represents an optionally substituted benzothien-2-yl group.

7. A pharmaceutical composition as claimed in claim 5 wherein Q represents an optionally substituted benzofuran-2-yl group.

8. A pharmaceutical composition as claimed in claim 7 wherein the said substituents are 1 to 3 halogen atoms.

* * * * *

UNITED STATES PATENT AND TRADEMARK OFFICE
CERTIFICATE OF CORRECTION

PATENT NO. : 5,004,751

DATED : April 2, 1991

INVENTOR(S) : Ei MOCHIDA, Kimihiro MURAKAMI, Kazuo KATO, Katsuaki KATO, Jun OKUDA, and Ichitomo MIWA It is certified that error appears in the above-identified patent and that said Letters Patent is hereby corrected as shown below:

Column 88, line 43 (claim 1), change "benzofuryl" to --benzo[b]furyl--; change "benzothienyl" to --benzo[b]thienyl--.

Column 88, line 57 (claim 2) change "thien-2-yl" to --[b]thien-2-yl--; change "toxic" to --non-toxic--.

Column 88, line 60 (claim 3) change "benzofu-" to --benzo[b]fu- --.

Column 89, line 12 (claim 5), change "benzofuryl" to --benzo[b]furyl--; change "benzothienyl" to --benzo[b]thienyl--.

Column 90, line 10 (claim 6), change "thien-2-yl" to --[b]thien-2-yl--.

Column 90, line 13 (claim 7), change "zofuran-2-yl" to --zo[b]furan-2-yl--.

Signed and Sealed this

Twenty-second Day of September, 1992

Attest:

DOUGLAS B. COMER

Attesting Officer     Acting Commissioner of Patents and Trademarks